US009539371B2

(12) United States Patent
Wen et al.

(10) Patent No.: US 9,539,371 B2
(45) Date of Patent: Jan. 10, 2017

(54) COATING AGENTS AND COATED ARTICLES

(71) Applicant: Innovative Surface Technologies, Inc., St. Paul, MN (US)

(72) Inventors: Jie Wen, St. Johns, FL (US); Kristin Taton, Little Canada, MN (US); Laurie Lawin, New Brighton, MN (US); William Knopke, Minneapolis, MN (US); Eric Guire, St. Paul, MN (US); Patrick Guire, Hopkins, MN (US)

(73) Assignee: INNOVATIVE SURFACE TECHNOLOGIES, INC., St. Paul, MN (US)

(*) Notice: Subject to any disclaimer, the term of this patent is extended or adjusted under 35 U.S.C. 154(b) by 15 days.

(21) Appl. No.: 14/749,815

(22) Filed: Jun. 25, 2015

(65) Prior Publication Data
US 2015/0359944 A1 Dec. 17, 2015

Related U.S. Application Data

(63) Continuation of application No. 13/518,337, filed as application No. PCT/US2010/061602 on Dec. 21, 2010, now abandoned.

(60) Provisional application No. 61/288,803, filed on Dec. 21, 2009.

(51) Int. Cl.
| C09D 137/00 | (2006.01) |
| A61L 31/10 | (2006.01) |
| C08F 8/30 | (2006.01) |
| C08F 8/42 | (2006.01) |
| C09D 131/00 | (2006.01) |
| A61L 31/02 | (2006.01) |
| A61L 31/06 | (2006.01) |
| A61L 31/14 | (2006.01) |
| A61L 31/16 | (2006.01) |
| A61L 33/00 | (2006.01) |
| B05D 3/06 | (2006.01) |

(52) U.S. Cl.
CPC .............. *A61L 31/10* (2013.01); *A61L 31/022* (2013.01); *A61L 31/06* (2013.01); *A61L 31/14* (2013.01); *A61L 31/16* (2013.01); *A61L 33/0005* (2013.01); *B05D 3/06* (2013.01); *C08F 8/30* (2013.01); *C08F 8/42* (2013.01); *C09D 131/00* (2013.01); A61L 2300/404 (2013.01); A61L 2300/42 (2013.01); A61L 2400/10 (2013.01); A61L 2420/02 (2013.01); A61L 2420/08 (2013.01); Y10T 428/3175 (2015.04); Y10T 428/31507 (2015.04); Y10T 428/31511 (2015.04); Y10T 428/31573 (2015.04); Y10T 428/31598 (2015.04); Y10T 428/31663 (2015.04); Y10T 428/31667 (2015.04); Y10T 428/31721 (2015.04); Y10T 428/31797 (2015.04); Y10T 428/31855 (2015.04); Y10T 428/31884 (2015.04); Y10T 428/31909 (2015.04); Y10T 428/31913 (2015.04); Y10T 428/31928 (2015.04)

(58) Field of Classification Search
CPC ............. C09D 135/00; C08F 8/42; B05D 3/06
See application file for complete search history.

(56) References Cited

U.S. PATENT DOCUMENTS

| 2,601,337 | A | 6/1952 | Smith-Johannsen |
| 3,088,847 | A | 5/1963 | Pines |
| 3,794,736 | A | 2/1974 | Abbott et al. |
| 3,971,884 | A | 7/1976 | Meeks et al. |
| 4,395,462 | A | 7/1983 | Polmanteer |
| 4,617,078 | A | 10/1986 | Takahashi et al. |
| 4,981,988 | A | 1/1991 | Ichinohe et al. |
| 5,002,582 | A | 3/1991 | Guire et al. |
| 5,443,455 | A | 8/1995 | Hergenrother et al. |
| 5,512,329 | A | 4/1996 | Guire et al. |
| 5,714,360 | A | 2/1998 | Swan et al. |
| 5,741,551 | A | 4/1998 | Guire et al. |
| 5,749,837 | A | 5/1998 | Palermo et al. |
| 5,769,796 | A | 6/1998 | Palermo et al. |
| 5,888,656 | A | 3/1999 | Suzuki et al. |
| 5,997,517 | A | 12/1999 | Whitbourne |
| 6,254,634 | B1 | 7/2001 | Anderson et al. |
| 6,278,018 | B1 | 8/2001 | Swan |
| 6,465,178 | B2 | 10/2002 | Chappa et al. |
| 6,465,525 | B1 | 10/2002 | Guire et al. |
| 6,514,734 | B1 | 2/2003 | Clapper et al. |
| 6,689,473 | B2 | 2/2004 | Guire et al. |
| 6,773,888 | B2 | 8/2004 | Li et al. |

(Continued)

FOREIGN PATENT DOCUMENTS

| WO | 0034410 A1 | 6/2000 |
| WO | 2005035637 A1 | 4/2005 |

(Continued)

OTHER PUBLICATIONS

International Search Report for corresponding International Patent Application No. PCT/US2010/061602, completed Mar. 17, 2011 (4 pages).
Abbasi, Farhang et al., "Modification of polysiloxane polymers for biomedical applications: a review," Polym. Int. 50:1279-1287 (2001).
Barbey, R. et al., "Polymer Brushes via Surface-Initiated Controlled Radical Polymerization: Synthesis, Characterization, Properties, and Applications," Chem. Rev. 109:5437-5527 (2009).
Gann, J.P., et al., "A versatile method for grafting polymers on nanoparticles," Langmuir 24:5319-5323 (2008).
Keana, John F.W. et al., "New Reagents for Photoaffinity Labeling: Synthesis and Photolysis of Functionalized Perfluorophenyl Azides," J. Org. Chem. 55:3640-3647 (1990).

(Continued)

*Primary Examiner* — Kuo-Liang Peng
(74) *Attorney, Agent, or Firm* — Weaver Legal and Consulting LLC; Karrie Gemignani Weaver

(57) ABSTRACT

The invention describes novel coating agents that include a polymer, one or more latent reactive groups and one or more noncovalent linking groups, the noncovalent linking groups selected to interact with a substrate to which the coating agent is applied.

20 Claims, 3 Drawing Sheets

(56) References Cited

U.S. PATENT DOCUMENTS

| | | | |
|---|---|---|---|
| 6,808,738 | B2 | 10/2004 | DiTizio et al. |
| 7,736,689 | B2 | 6/2010 | Chappa et al. |
| 7,772,393 | B2 | 8/2010 | Guire et al. |
| 7,943,234 | B2 | 5/2011 | Lawin et al. |
| 7,989,619 | B2 | 8/2011 | Guire et al. |
| 2007/0054127 | A1 | 3/2007 | Hergenrother et al. |
| 2008/0208334 | A1 | 8/2008 | Jinkerson et al. |
| 2008/0312315 | A1 | 12/2008 | Daniloff et al. |
| 2009/0092843 | A1 | 4/2009 | Arlt et al. |
| 2010/0227077 | A1 | 9/2010 | Wen et al. |

FOREIGN PATENT DOCUMENTS

| | | | |
|---|---|---|---|
| WO | 2007056338 A2 | | 5/2007 |
| WO | 2007097614 A1 | | 8/2007 |
| WO | 2008 103668 | * | 8/2008 |
| WO | 2008103668 A2 | | 8/2008 |
| WO | 2010028104 A1 | | 3/2010 |
| WO | 2010033482 A1 | | 3/2010 |

OTHER PUBLICATIONS

"Plastics," Concise Encyclopedia of Polymer Science and Engineering, Kroschwitz, ed., John Wiley and Sons, pp. 462-464 (1990).

Lee, Moo-Yeal et al., "Multienzyme Catalysis in Microfluidic Biochips," Biotechnology and Bioengineering, 83(1), pp. 20-28 (2003).

Makamba, Honest et al., "Surface modification of poly(dimethylsiloxane) microchannels," Electrophoresis 24:3607-3619 (2003).

"Principles of Polymerization," 2nd edition, Odian G., John Wiley and Sons, pp. 201-204 (1981).

Ohno, Kohji et al., "A Versatile Method of Initiator Fixation for Surface-Initiated Living Radical Polymerization on Polymeric Substrates," Macromolecules 43:5569-5574 (2010).

Roth, Jan et al., "Surface Functionalization of Silicone Rubber for Permanent Adhesion Improvement," Langmuir 24:12603-12611 (2008).

Werner et al., "Maleic Anhydride Copolymers—A Versatile Platform for Molecular Biosurface Engineering," Biomacromolecules, 2003, 4, pp. 1072-1079.

Wu et al., "Viscosity-Molecular Weight Relationship for Aminopropyl-Terminated poly(dimethylsiloxane)," Journal of Applied Polymer Science, 2001, 80, pp. 975-978.

Yan, M. et al., "Covalent Immobilization of Ultrathin Polymer Films by Thermal Activation of Perfluorophenyl Azide," Chem. Mater. 16:1627-1632 (2004).

* cited by examiner

COATING AGENTS AND COATED ARTICLES

CROSS REFERENCE TO RELATED APPLICATIONS

This application is a continuation of application Ser. No. 13/518,337, filed Jun 21, 2012, which is a Section 371 National Stage Application of International Application No. PCT/US2010/061602, filed Dec 21, 2010 and published as WO 2011/084811 on Jul 14, 2011, which claims priority from U.S. Provisional Application No. 61/288,803, filed Dec 21, 2009, the contents of which are incorporated herein in their entirety for all purposes.

This invention was made with government support under Grant No. 1R43HL093928-01A1, awarded by the National Institutes of Health. The government has certain rights in the invention.

FIELD OF THE INVENTION

Coating agents useful for application to substrates fabricated of materials such as silicone, stainless steel, polyethylene, and the like, are described. In some aspects, the coating agents are useful as surface primer agents, wherein they can provide a base coating to which additional coating layers can be applied. In other aspects, the coating agents can themselves provide desired features to a substrate surface. Articles are also described that include the coating agents on a surface.

BACKGROUND

Medical articles can be fabricated from a number of materials. For example, some common materials utilized to fabricate medical articles include metals and alloys, ceramics, glasses, glass-ceramics, polymeric materials, composites, cements, nonwovens and fabrics. The environment of the human body is surprisingly hostile and aggressive; therefore, selection of materials to be used in the human body involves consideration of such factors as material properties, application of the medical article, duration of residence within the body, and the like. Common polymeric materials used in the human body include silicones and other plastics, while metals include stainless steels, cobalt-chromium alloys, titanium and titanium alloys, shape memory alloys and tantalum.

It can be desirable to modify the surface of a medical article to impart desirable properties to the surface (such as lubricity, biocompatibility, antimicrobial action and the like), to release bioactive agents (such as drugs) over time, to render the medical article more visible to imaging systems, and the like.

Poly(dimethyl siloxane) (PDMS) belongs to a group of polymeric organosilicon compounds that are commonly referred to as silicones. Some applications of silicones include contact lenses, medical devices, elastomers, caulking, lubricating oils, and heat-resistant tiles. Silicones have been widely used in biomedical applications because of such material properties as excellent flexibility, durability, and bioinertness. However, surface modification of silicones is often needed to achieve desirable surface properties for various applications. Modification of silicone surfaces has proven challenging due to the material's extremely low surface reactivity and surface energy. To complicate the matter further, silicones usually contain high amounts of low-molecular weight components having high mobility in the polymer bulk and high tendency to migrate to the surface. This in turn can lead to a transient modification effect for only a few hours (hydrophobic recovery).

BRIEF SUMMARY OF THE INVENTION

In a first general aspect, coating agents are described for providing a priming or base coating layer on a material surface. Also described are methods of preparing such coating agents and methods of using such agents to coat a surface, such as the surface of an implantable medical article. In further aspects, the disclosure describes material surfaces coated with such coating agents, as well as methods of making and using such material surfaces and resultant articles. Such "primer" compositions can facilitate the use of additional coating "layers" of either the same and/or different compositions.

Accordingly, coating agents are described that comprise at least three main components, namely polymer, one or more latent reactive groups, and one or more noncovalent linking groups, wherein the noncovalent linking groups are selected to interact with a substrate to which the coating agent is applied. Latent reactive groups can be pendent from the polymer backbone. Noncovalent linking groups can be pendent from the polymer backbone and/or included within the polymer backbone. In some aspects, the latent reactive groups and noncovalent linking groups are different from one another.

In some embodiments, a coating agent can comprise: (a) a polymer including a polymaleic acid derivative, (b) one or more latent reactive groups, and (c) one or more noncovalent linking groups, the noncovalent linking groups selected to interact with a substrate to which the coating agent is applied. In some aspects, the polymer is a copolymer. Latent reactive groups can be pendent from the polymer backbone. Noncovalent linking groups can be pendent from the polymer backbone and/or included within the polymer backbone.

The coating agents can be used alone to provide a coated surface, or in combination with additional coating layers. In some embodiments, the coating agent comprises a surface primer agent. One or more additional coating compositions can be applied to the surface primer agent, thereby providing a final coated product. Alternatively, coating agents can themselves provide desirable properties to a material surface. In these embodiments, subsequent coating layers of the same and/or different compositions are not required to provide a final desired feature or property to the surface. Instead, the desirable features or properties are provided by components of the coating agents themselves.

Coated articles are also described herein. In some aspects, articles can comprise a substrate including silicon, and a coating disposed on a surface of the substrate, the coating comprising: (a) a polymer, (b) one or more latent reactive groups that are pendent from the polymer, and (c) one or more noncovalent linking groups, wherein the noncovalent linking groups are selected to interact with the substrate. In other aspects, the substrate can be fabricated of other materials (for example, polymeric materials such as polyethylene; metals such as stainless steel or aluminum; or the other materials), and the noncovalent linking groups can be selected to interact with the substrate material. The polymer can include a polymaleic acid derivative, such as a derivatized poly(alkene-co-maleic anhydride). In some embodiments, the polymer is a copolymer. The noncovalent linking groups can be selected from siloxanes. $C_4$-$C_{20}$ alkyl groups, polyamides, phenolics, catechols, polyethylene glycol, polyethylene glycols, acrylates, polyacrylates, polyurethanes, polycarbonates, polyesters, polyethylenes, polypropylenes or polyethers, or a combination of any of these.

Methods of making coating agents, as well as methods of using the coating agents to modify a surface of a substrate are also described. Further embodiments will be apparent upon review of the disclosure.

DETAILED DESCRIPTION

Figure 1:
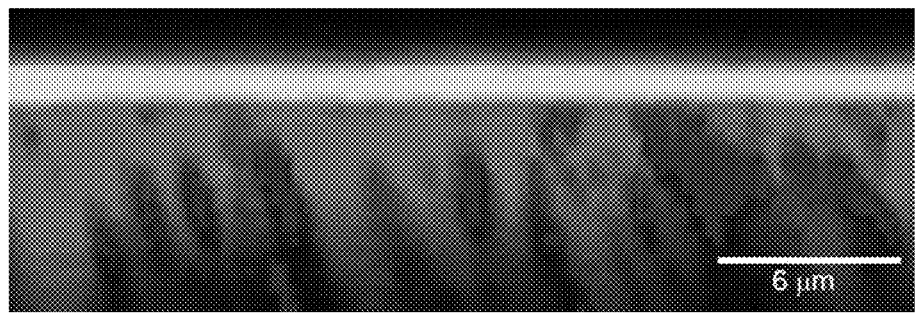
FIG. 1 shows confocal Raman microscopy of a coating layer on silicone catheter.

The embodiments of the present invention described herein are not intended to be exhaustive or to limit the invention to the precise forms disclosed. Rather, the embodiments are chosen and described so that others skilled in the art can appreciate and understand the principles and practices of the present invention. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that the inventors are not entitled to antedate any publication and/or patent, including any publication and/or patent cited herein.

In the specification and in the claims, the terms "including" and "comprising" are open-ended terms and should be interpreted to mean "including, but not limited to . . . " These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

As used herein, the term "layer" or "coated layer" refers to a layer of one or more coated materials of sufficient dimensions (for example, thickness and area) for its intended use over the entire, or less than the entire, portion of an article surface. A "coating" as described herein can include one or more "coated layers," each coated layer including one or more coating components. In some aspects, inventive coatings can consist of a single coated layer of polymeric material, for example, a coating agent.

In some aspects, inventive coating agents can create a durable and robust coating on substrates which can otherwise be difficult to coat due to low surface energy and/or lack of reactive groups on the surface of the substrate. In some embodiments, the durable and robust coating can last for weeks or months. Additionally, embodiments of the present invention also include surface treatments which are durable after application of the coating agents to the substrate.

As used herein, the term "durability" refers to the wear resistance of a coating, or the ability of a coating to be maintained on a substrate surface when subjected to forces typically encountered during use (for example, normal force, shear force, and the like). A more durable coating is less easily removed from a substrate by abrasion. Durability of a coating can be assessed by subjecting a substrate (such as a medical device) to conditions that simulate use conditions. In accordance with inventive concepts, coatings can be formed on a device surface in such a manner as to withstand the effect of normal forces or shear forces that may be encountered in some aspects of the invention during use of the coated article. In these cases, such forces could otherwise result in delamination of the coating from the substrate surface.

In contrast, surface coating of silicones, such as poly (dimethylsiloxane) (PDMS), via conventional pretreatments such as plasma treatment, corona discharge and/or UV-irradiation can be fleeting and transient. These conventional pretreatments are typically associated with a phenomenon called hydrophobic recovery, which can be caused by the reorientation of polar groups from the surface to the bulk phase, by the reorientation of nonpolar groups from the bulk to the surface, or by the diffusion of low molecular weight silicone fluid from the bulk to the surface. The high mobility of the silicone chains can cause a hydrophobic recovery over a short time scale (for example, minutes to days).

Advantageously, a substrate coated with inventive coating agents described herein can retain physical, chemical or biological characteristics longer than comparative substrates coated with conventional surface primers or coating agents. Generally, a polymeric composition including a latent reactive group and a non-covalent linking group can be applied to a substrate. The non-covalent linking group can associate with the surface of the substrate. The latent reactive group of the polymeric composition can be activated with an external energy source, such as actinic or thermal energy, to form a covalent bond between the coating agent and the substrate, and among polymer chains of the coating agent. In some embodiments a polymeric composition wherein the latent reactive group is covalently bonded to the polymer provides for more robust and durable coating layer than when a "free" latent reactive group is mixed with the coating formulation.

In other embodiments, a silicon-containing substrate can be coated with a coating agent in accordance with inventive concepts without the need for pretreatment of the silicon substrate. A polymeric composition including a latent reactive group and a non-covalent linking group including a siloxane group can associate with a surface of the silicon material. The non-covalent linking group can associate with the surface of the silicon substrate. The latent reactive groups on the coating reagent can be activated with actinic energy or thermal energy, thus forming covalent bonds between the coating agent and the substrate, and among polymer chains of the coating agent. This can result in a robust and durable coated layer on the silicon substrate. Optionally, the coated layer can then be further reacted with another coating layer, or an overcoat layer to impart desirable characteristics, for example such as lubricity or wettability, to the substrate.

When applied, inventive coating agents can form a coated layer on a surface of a support material. This layer, in turn, can be stably retained upon the surface and can serve as an attachment site for binding additional compositions (such as polymeric formulations, active agents, and the like) to the surface. The word "layer," as used herein, will refer to a coating of sufficient dimensions (such as thickness and coverage area) for its intended use (such as over all, or a portion) of a support material surface.

Optionally, the coating agents can function as a surface priming agent. In these embodiments, subsequent coating compositions can be applied to achieve a desired surface characteristic, such as, for example, hydrophilicity, hydrophobicity, and the like. Such final coatings can in turn provide desired characteristics to the substrate. For example, a superhydrophobic coating can provide passivating coatings, passivating against proteins such as BSA and serum, and cellular adhesion including HeLa cells and whole blood, or microbial adsorption (such as *Staphylococcus aureus*).

As used herein. "passivation" is the process of making a surface "passive," that is, a surface film or coating is created that results in a reduction of biological responses when exposed to biological materials (for example, reduction of protein adsorption or reduction of cellular responses mediating inflammation). A passivating coating forms a surface having improved biological passivation as compared to the uncoated material, when exposed to conditions of use (for example, in a human body).

Optionally, the coating agents can further comprise one or more active agents. Such active agents can be included to provide desired properties to a final coated article, such as a passivating surface, antimicrobial properties, or the like. In such embodiments, a coated layer in accordance with the invention can provide passivating features to a substrate without application of additional coating layers. In some such embodiments, the coating agent can include a polymer, one or more one or more latent reactive groups, one or more noncovalent linking groups, and one or more passivating groups. The noncovalent linking groups can be selected to interact with a substrate to which the coating agent is applied.

In still further aspects, the active agent can comprise an initiator. In accordance with these aspects, a coating agent can include a polymer, one or more latent reactive groups, one or more noncovalent linking groups, and an initiator group. The initiator group can be selected to initiate polymerization from a coated surface. The initiator groups provide a site for reaction with monomers to produce covalently attached polymeric units by "grafting from" techniques or, alternately, for reaction with prefabricated polymers.

Various features of the coating agents will now be described in more detail.

Inventive coating agents can be provided to a wide variety of substrates. In some aspects, the coating agents can be utilized in connection with substrates that are otherwise difficult to coat.

The particular form of the substrate is not critical. In accordance with inventive aspects, the substrates can be provided in a number of different formats. Illustrative substrates include, for example, solid tangible surfaces, particles, solution polymers, emulsions, or suspensions.

Illustrative solid tangible surfaces include surfaces of medical devices, including implantable medical devices, medical devices for temporary insertion into a patient's body, medical tubing, and the like. Inventive coating agents can also be applied to substrates outside the implantable medical device field, as will be apparent from the variety of materials that can be coated with the inventive coating agents.

Suitable materials for fabrication of solid tangible surfaces include materials commonly used to fabricate implantable medical articles. The solid tangible surface is optionally intended to function in contact with tissue and/or fluids of the body. Examples of suitable support materials include those materials commonly used to fabricate implantable medical articles such as metals, minerals or ceramics, carbon-based materials, and polymers.

Suitable metals include, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses. Illustrative carbon-based materials include pyrolytic carbon, as well as carbon materials obtained by thermal degradation (thermolysis, pyrolysis) or organic compounds, as well as materials obtained by physical vapor deposition (PVD) techniques.

As will be appreciated in light of this disclosure, inventive coating agents can be particularly useful in connection with solid tangible surfaces fabricated of silicone (poly(dimethylsiloxane)). However, the inventive concepts can also be applicable with a number of other polymeric materials. In some aspects, the coating agents can be useful in connection with substrates fabricated of a synthetic or natural polymer. For example, the substrate can be fabricated from synthetic polymer such as Parylene™ (tradename for a variety of chemical vapor deposited poly(p-xylylene) polymers), polyamides (such as polyether block amides such as PEBAX™), polyesters, polyethylenes, polyethylene terephthalates (PET), poly(meth)acrylates, polyacetates, polyvinylacetates, sulfonic acid-substituted polymers, polyacrylamide polyethylene glycols, polyethyleneimines, polylactic acids, polyglycolic acids, polylactide-co-glycolides, polyvinyl alcohols, polyvinyl pyrrolidones, quaternary amine-substituted polymers, conductive polymers (for example, polyvinylpyridine, polyacetylenes, polypyrroles), poly-(p-pheyleneterephthalamides), polyphosphazenes, polypropylenes, polyetetrafluoroethylenes, polysiloxanes, inorganic synthetic elastomers, organic polymers, or copolymers thereof or combinations of any of these. In other embodiments, the substrate can be formed from natural polymers such as polysaccharides, proteins, nucleic acids or organic polymers.

In some aspects, a suitable substrate can be fabricated of a plastic material. Exemplary plastics include silicones, polyolefins, vinyl polymers, polystyrenes, polyacrylates (including polymethacrylate), poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose-based plastics, and rubber-like plastics, providing surfaces that can be modified as described herein. See generally, "Plastics", pp. 462-464, in Concise Encyclopedia of Polymer Science and Engineering, Kroschwitz, ed., John Wiley and Sons, 1990. Illustrative polyolefins include polyethylene, such as high density polyethylene (HDPE), polytetrafluoroethylene, and the like, as well as polypropylene and the like.

The coating agents and methods can also be used to provide coatings on inorganic substrates such as glass, ceramics and metals, for example, aluminum, stainless steel and noble metals. In such embodiments, the surfaces themselves can be derivatized, directly or via intermediate coatings, so as to provide suitable latent reactive groups or suitable targets for coupling with latent reactive groups.

Optionally, the coating agent can be provided to a substrate that has been pretreated. Pretreatment of the substrate can include treatment of one or more surfaces of the substrate to make groups on the surface of the treated substrate which would not otherwise exist on the non-pretreated substrate. The groups are created on the surface of the treated substrate to meet a particular need of the surface of the substrate, such as but not limited to, creating groups on the substrate which can be reactive toward groups on the coating agent layer. In other embodiments, other particular needs include attachment of biologically active molecules. In these particular aspects, such pretreatments can include, but are not limited to, chemical pretreatments, biological pretreatments, physical pretreatments (such as etching) or combinations thereof.

In some embodiments chemical pretreatment of substrates can include, by example, washing with strong acid. In other embodiments chemical pretreatment can include washing the surface of the substrate with a strong base. In other embodiments, physical pretreatments can be used. Physical pretreatments include, but are not limited to flame pretreatment, plasma pretreatment, corona pretreatment, or combinations thereof.

Other pretreated surfaces can include Parylene™ coated surfaces, and silylated surfaces of glass, ceramic, or metal.

In yet other embodiments the substrate surface can require no pretreatment before coating with the coating agent. The lack of pretreatment can be advantageous. In accordance with inventive aspects, before pretreatment, the substrate surface can be hydrophobic and can be primed without pretreatment. In other aspects, before pretreatment, the substrate surface can be hydrophilic and can be coated with inventive coating agents without pretreatment.

In some embodiments, the non-pretreated surface of the substrate can be coated with a coating agent containing a latent reactive group, a non-covalent linking group and a polymer. The non-covalent linking group can act to associate with the substrate, and actinic energy can be applied to the coated substrate to activate the latent reactive group. In certain instances the latent reactive group can form a covalent bond between the coating agent and the substrate.

Other embodiments can include a substrate which includes one or more latent reactive groups covalently bonded thereto. A coating agent containing non-covalent linking group and a polymer can be coated on the substrate which has one or more latent reactive groups. The non-covalent linking group can act to associate with the substrate which contains a latent reactive group. External energy can be applied to the coated substrate to activate the latent reactive group and, in some cases, form a covalent bond between the coating agent and the substrate.

In yet other embodiments, both the coating agent and the substrate can include independently chosen latent reactive groups. These latent reactive groups can be activated with actinic energy, thus forming a covalent bond between the substrate and the coating agent.

The coating agents can include one or more non-covalent linking groups. In certain embodiments, the non-covalent linking group can be selected to provide an advantageous interaction, association, attraction, or an affinity with the substrate. The term "non-covalent linking group" is a phrase that characterizes the occurrence of an interaction, attraction, or affinity with the substrate and moieties on or in embodiments of the coating agent. The terms or phrases non-covalent linking group, interaction group, attraction group, or affinity group can be used interchangeably. The non-covalent linking group can interact with the substrate during contact of the substrate with the non-covalent linking group, or when the non-covalent linking group is brought within sufficient proximity to a substrate. Optionally, the substrate interacting with the non-covalent linking group can be a pretreated substrate. However, as will be apparent from review of this disclosure, such substrate pretreatment is not required. In some aspects, the non-covalent linking group can also include a functional group that can reversibly interact with the substrate, for example, through reversible non-covalent interactions.

In an embodiment, the non-covalent linking group can be functionalized with moieties that can engage in non-covalent interactions with the substrate. For example, the non-covalent linking group can include functional groups such as an ionic group, a group that can hydrogen bond, or a group that can engage in van der Waals or other hydrophobic interactions. Such functional groups can include silane groups siloxane groups, cationic groups, anionic groups, lipophilic groups, amphiphilic groups, and the like.

The present methods and compositions can employ a non-covalent linking group including a charged moiety. Suitable charged moieties include positively charged moieties and negatively charged moieties. Suitable positively charged moieties include amines, quaternary ammonium moieties, sulfonium, phosphonium, ferrocene, and the like. Suitable negatively charged moieties (for example, at neutral pH in aqueous compositions) include carboxylates, phenols substituted with strongly electron withdrawing groups (for example, tetrachlorophenols), phosphates, phosphonates, phosphinates, sulphates, sulphonates, thiocarboxylates, and hydroxamic acids.

The present methods and compositions can employ a non-covalent linking group including a group that can hydrogen bond, either as donor or acceptor (for example, a second hydrogen bonding group). For example, the non-covalent linking group can include one or more carboxyl groups, amine groups, hydroxyl groups, carbonyl groups, or the like. Ionic groups can also participate in hydrogen bonding.

In some aspects, a non-covalent linking group can comprise a catechol-based group that is capable of interacting with a surface. For example, a non-covalent linking group can comprise catecholamine (that is, dopamine, or 4-(2-aminoethyl)benzen-1,2-diol).

The present methods and compositions can employ a non-covalent linking group including a lipophilic moiety (for example, a second lipophilic moiety). Suitable lipophilic moieties include one or more branched or straight chain $C_{6-36}$ alkyl, $C_{8-24}$ alkyl, $C_{12-24}$ alkyl, $C_{12-18}$ alkyl, or the like; $C_{6-36}$ alkenyl, $C_{8-24}$ alkenyl, $C_{12-24}$ alkenyl, $C_{12-24}$ alkenyl, or the like, with, for example, 1 to 4 double bonds; $C_{6-36}$ alkynyl, $C_{8-24}$ alkynyl, $C_{12-24}$ alkynyl, $C_{12-18}$ alkynyl, or the like, with, for example, 1 to 4 triple bonds; chains with 1-4 double or triple bonds; chains including aryl or substituted aryl moieties (for example, phenyl or naphthyl moieties at the end or middle of a chain); polyaromatic hydrocarbon moieties; cycloalkane or substituted alkane moieties with numbers of carbons as described for chains; combinations or mixtures thereof; or the like. The alkyl, alkenyl, or alkynyl group can include branching; within chain functionality like an ether group; terminal functionality like alcohol, amide, carboxylate or the like; or the like. In an embodiment the non-covalent linking group includes or is a lipid, such as a phospholipid.

The non-covalent linking group can form as a result of interaction with an alcohol, phenol, thiol, amine, carbonyl, or like group present on the substrate. The interaction of the non-covalent linking group and the substrate can be formed by the reversible interactions. The non-covalent linking group can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

For example, suitable non-covalent linking groups can include: the functional group or groups participating in or formed by the reversible interaction with the substrate, and a non-covalent linking group moiety. A non-covalent linking group can include about 4 to about 48 carbon or heteroatoms, about 8 to about 14 carbon or heteroatoms, about 12 to about 24 carbon or heteroatoms, about 16 to about 18 carbon or heteroatoms, about 4 to about 12 carbon or heteroatoms, about 4 to about 8 carbon or heteroatoms, or the like. In an embodiment, the non-covalent linking group can be an alkyl chain of 16 carbons or a hexadecyl chain or group of carbons. The non-covalent linking group can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, mixtures thereof, or like moiety.

In some aspects, the non-covalent linking group can include a lipophilic moiety and, optionally, one or more moieties for forming a hydrogen bond or an ionic interaction. In such embodiments, the lipophilic moiety can have about 4 to about 48 carbons, about 8 to about 14 carbons, about 12 to about 24 carbons, about 16 to about 18 carbons, or the like. In such embodiments, the non-covalent linking group can include about 1 to about 8 reversible bond/interaction moieties or about 2 to about 4 reversible bond/interaction moieties. Suitable non-covalent linking groups have structures such as $(CH_2)_n COOH$, with n=12-24, n=17-24, or n=16-18.

Non-covalent linking groups of the coating agent can be selected to associate or interact with the substrate or substrates to which the coating agent is applied. Selection of non-covalent linking groups for a particular coating agent can thus take into account such factors as the substrate to be coated, other components of the coating agent to be utilized (such as the polymer and latent reactive group(s) to be included in the coating agent), solvent systems, reaction conditions, and the like. When considering the substrate to be coated, typical factors taken into account include the design of the substrate (such as whether the substrate is provided with a planar surface, or is provided as a multi-faceted construction that is typical in medical device applications), the material used to fabricate the substrate (such as polymer, metal, and the like as described herein), and the like. Consideration of the latent reactive group(s) to be included in the coating agent can involve taking into account the type of external stimuli to be used to transform the latent reactive group to an activated state (such as light or thermal energy).

Illustrative non-covalent linking groups include siloxane groups, polyamides, $C_4$-$C_{20}$ alkyl groups, polyethylene glycol, and polyethylene glycols, acrylates, polyacrylates, polyurethanes, polycarbonates, polyesters, polyethylenes, polypropylenes and polyethers. In yet other embodiments the non-covalent linking group can be the reaction product of 3-aminopropylmethylbis(trimethylsiloxy)silane with the anhydride group of poly(maleic anhydride-alt-1-octadecene) to form a pendent amide siloxane group represented by the following formula I,

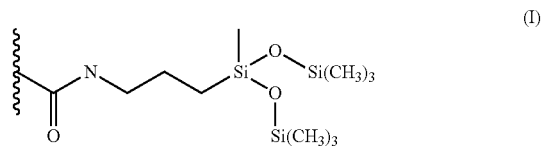

wherein wavy lines represent the polymer.

In some embodiments, the non-covalent linking group of the coating agent is pendent to the backbone of the polymer and interacts, associates, or has an affinity with the substrate, but the non-covalent linking group does not covalently bond with the substrate. Pendent groups can be, for example, a group that is branched from the polymer. Examples of pendent groups include, siloxane groups, carboxyl groups, quaternary amine groups and the like.

Covalent bonding of the coating agent to the substrate can occur through the activation of the latent reactive groups of the coating agent. The non-covalent linking group and the latent reactive groups of the coating agent can be chosen such that they are compatible with the substrate to be primed or coated. Compatibility includes, but is not limited to, the latent reactive group reacting with the substrate upon being subjected to activation energy. Compatibility further includes aspects such as wettability and hydrophobicity/hydrophilicity considerations of the coating agent. Thus the non-covalent linking group and covalent bonding can be compatible with one substrate system.

In other embodiments, the non-covalent linking group can be part of or incorporated into the polymer component of the coating agent. A non-covalent linking group can be, for example, part of the backbone of the polymer wherein the non covalent linking group would not be pendent from the polymer component of the coating agent. For example, non-pendent noncovalent linking groups can comprise an alkyl chain of a polymer. An example of an alkyl chain non-covalent linking group being part of a polymer, for example, in the polymer backbone, is an alkene, such as octadecene.

In some embodiments the interaction of the non-covalent linking group and the substrate can be independently attributed to many different factors. By example, some of the factors independently contributing to the interaction of the non-covalent linking group with the substrate include, but are not limited to, (i) charge-charge interactions, (ii) hydrogen bonding interactions, (iii) dipole interactions, (iv) fluctuating dipole interactions, (v) counter ion effects, and (vi) hydrophobic/hydrophilic interactions.

Charge-charge interactions can be between cationic groups and anionic groups and can be very strong. Charge-charge interactions are known to fall off slowly as distance between the charge centers increases. An example of a charge-charge interaction is that between an amine group and a sulfonate group.

Dipole interactions can arise from molecules that have unlike atoms within their structure wherein the unlike atoms have differing electronegativities. An example of a dipole interaction is interactions between carbonyl groups.

Fluctuating dipole interactions can arise from molecules which are located near to each other allowing for oscillator coupling. The resulting attractive interaction is known as dispersive interactions and can occur even between non-polar molecules. The strength of the interaction can be largely dependent upon the polarizability of the two molecules. An example of fluctuating dipole interactions can be the interaction between aromatic groups. In other embodiments, an example of a fluctuating dipole interaction can be between hydrocarbon groups.

Hydrogen bonding interaction can arise when a hydrogen atom simultaneously bonds to two other atoms. A hydrogen bond is not an acid-base reaction. In a hydrogen bond interaction the hydrogen is not transferred to one of the two other bonding atoms, as the hydrogen is in an acid-base reaction, but rather the hydrogen bonds with the two atoms. An example of a hydrogen bonding interaction can be represented as in Formula II.

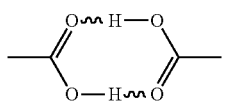

II

More complete details of the various interactions described above are described in March's, Advanced Organic Chemistry: Reactions, Mechanisms, and Structure, Jerry March et al.

In accordance with inventive principles, coating agents include a polymer, one or more latent reactive groups, and one or more non-covalent linking groups. Features of the latent reactive group(s) will now be described. The latent reactive group can be a photoreactive group that can become chemically reactive when exposed to an appropriate actinic energy source. As used herein, the phrases "latent photoreactive group" and "photoreactive group" are used interchangeably and refer to a chemical moiety that can be sufficiently stable to remain in an inactive state (ground state) under ambient storage conditions but that can undergo a transformation from the inactive state to an activated state when subjected to an appropriate reaction conditions. Similarly, the phrases "latent thermally reactive" and "thermoreactive group" can be used interchangeably and in the same sense. For such latent reactive groups, appropriate reaction conditions may include exposure to an external energy source. Suitable external energy sources include light sources, (such as UV or ultraviolet light) or heat sources. Other illustrative reaction conditions may include chemical reaction conditions, for example, the presence of a oxidizers and reducing agents (redox pairs).

Generally, photoreactive groups respond to specific applied external stimuli to undergo active specie generation with resultant covalent bonding to an adjacent chemical structure, for example, as provided by the same or a different molecule. Suitable photoreactive groups are described, for example, in U.S. Pat. No. 5,002,582 (Guire et al.).

Photoreactive groups can be chosen to be responsive to various types of actinic energy. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In an embodiment, each photoreactive group can extract a hydrogen atom from an alkyl group on either of the non-covalent linking group, the substrate, or a combination thereof. A covalent bond can form between the photoreactive group and the non-covalent linking group and between the photoreactive group, the substrate and between the photoreactive group agent and other intramolecular and intermolecular polymer groups. By covalently bonding to both groups, the photoreactive group can promote adhesion and/or increase coupling strength of the coating agent.

In some embodiments, the photoreactive group can be an aryl ketone, such as acetophenone, benzophenone, anthrone, and anthrone-like heterocycles (heterocyclic analogs of anthrone such as those having N, O, or S in the 10-position), or their substituted (for example, ring substituted) derivatives. Examples of aryl ketones include heterocyclic derivatives of anthrone, including acridone, xanthone, and thioxanthone, and their ring substituted derivatives. Other suitable photoreactive groups include quinones such as, for example anthraquinone.

The functional groups of such aryl ketones can undergo multiple activation/inactivation/reactivation cycles. For example, benzophenone can be capable of photochemical excitation with the initial formation of an excited singlet state that undergoes intersystem crossing to the triplet state. The excited triplet state can insert into carbon-hydrogen bonds, for example but not limited to that of a substrate, by abstraction of a hydrogen atom (from a polymeric coating layer, for example), thus creating a radical pair. Subsequent collapse of the radical pair leads to formation of a new carbon-carbon bond. If a reactive bond (for example, carbon/hydrogen) is unavailable for bonding, the ultraviolet light-induced excitation of the benzophenone group can be reversible and the molecule returns to ground state energy level upon removal of the energy source. Photoreactive aryl ketones such as benzophenone and acetophenone can undergo multiple reactivations in water and thus provide increased coating efficiency.

The azides constitute another class of photoreactive groups and include arylazides such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate. Diazo compounds are also thermally reactive groups.

Other photoreactive groups include the diazirines (—$CHN_2$) such as 3-trifluoromethyl-3-phenyldiazirine; and ketenes CH=C=O) such as ketene and diphenylketene.

In an embodiment, the photoreactive group can be non-ionic. In one embodiment, the non-ionic photoreactive group includes the tetrakis(4-benzoylbenzyl ether) or the tetrakis (4-benzoylbenzyl ester) of pentaerythritol. In these aspects, one or more of the photoreactive groups can react with the substrate. The photoreactive group therefore attaches the coating agent to the substrate.

In some embodiments, the photoreactive group can be ionic. For example, in some embodiments, at least one ionic photoreactive group can be included in the coating agent. Any suitable ionic photoreactive group can be used. In some embodiments, the ionic photoreactive group can be a compound of Formula III:

$$X_1—Y—X_2$$ (III)

where Y is a radical containing at least one acidic group, basic group, or salt thereof and $X_1$ and $X_2$ are each independently a radical containing a latent photoreactive group.

The photoreactive groups can be the same as those described above for a non-ionic photoreactive group. Spacers, such as those described for the non-ionic photoreactive group, can be part of $X_1$ or $X_2$ along with the latent photoreactive group. In some embodiments, the latent photoreactive group includes an aryl ketone or a quinone.

In some embodiments of Formula III, Y can be a radical containing at least one acidic group or salt thereof. Such a photoreactive group can be anionic depending on the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic group includes a sulfonic acid or sulfonate group. Suitable counter ions include alkali, alkaline earths, ammonium, protonated amines, and the like.

For example, a compound of Formula III can have a radical Y that contains a sulfonic acid or sulfonate group; $X_1$ and $X_2$ contain photoreactive groups such as aryl ketones. Such compounds include 4,5-bis(4-benzoylphenylmethylencoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxyl)ethyl]-2-aminoethanesulfonic acid or salt, and the like. See U.S. Pat. No. 6,278,018 (Swan). The counter ion of the salt can be, for example, ammonium or an alkali metal such as sodium, potassium, or lithium.

In other embodiments of Formula III, Y can be a radical that contains a basic group or a salt thereof. Such Y radicals can include, for example, an ammonium, a phosphonium, or a sulfonium group. The group can be neutral or cationic depending on the pH of the coating composition. In some embodiments, the radical Y includes an ammonium group. Suitable counter ions include, for example, carboxylates, halides, sulfate, and phosphate.

For example, compounds of Formula III can have a Y radical that contain an ammonium group; $X_1$ and $X_2$ contain photoreactive groups that include aryl ketones. Such photoreactive groups include ethylenebis(4-benzoylbenzyldimethylammonium) salt, hexamethylenebis(4-benzoylbenzyldimethylammonium) salt, 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt, 4,4-bis(4-benzoylbenzyl)morpholinium salt, ethylenebis[(2-(4-benzoylbenzyldimethylammonio)ethyl)-4-benzoylbenzylmethylammonium]salt, and 1,1,4,4-tetrakis (4-benzoylbenzyl)piperazinediium salt. See U.S. Pat. No. 5,714,360. The counter ion can typically be a carboxylate ion or a halide. In one embodiment, the halide can be bromide.

In some embodiments, the latent reactive group can comprise a thermally reactive group. Thermal activation may be advantageous when exposure to UV light is not practical (for example the inner lumen of a tubular device) or is undesirable (for example when coating materials containing of UV light-sensitive components). Thermally reactive groups may also be advantageous in coatings exhibiting low transmission of UV light. Thermally reactive groups can include pairs of atoms having a heat sensitive (labile) bond between the atoms. Examples of such pairs of atoms include oxygen-oxygen (per-esters), nitrogen-oxygen, and nitrogen-nitrogen. Examples of thermally reactive groups useful in present embodiments include 4,4' azobis(4-cyanopentanoic acid) and analogs of benzoyl peroxide. External energy sources to produce thermal energy can be used to activate a thermally reactive group.

In some embodiments, the latent reactive group can include one or more nitrenogenic groups. For example, a latent reactive group can comprise a perhalophenylazide (PHPA), such as perfluorophenylazide (PFPA). A "nitrenogenic group" is a chemical moiety that becomes a nitrene group when exposed to a reaction-energy source. An azido group is an example of a nitrenogenic group. In turn, a "nitrene group" (also generally termed "nitrene" or "nitrene intermediate") is a particular form of nitrogen group regarded as the nitrogen analog of carbenes. Like carbenes, nitrenes are generally regarded as intermediates that are highly reactive and may not be isolatable under ordinary conditions. Important nitrene reactions include (but are not limited to) addition or insertion into C—H, N—H, O—H, and C—C bonds (single and double).

Perfluorophenylazide can behave as a photochemically reactive or thermally reactive group, which generates perfluorophenyl nitrenes that undergo C—H/N—H insertion and alkene addition reactions. The phenyl group fluorine atoms increase the lifetime of the nitrene and favor desirable crosslinking insertion with moderate to high efficiency instead of undesirable ring expansion. Insertion reactions are reported to take place at temperatures typically 130° C. or greater. Perfluorophenylazides typically can be derived from 4-azido-2,3,5,6-tetrafluorobenzoic acid.

When the latent reactive group comprises one or more photochemically reactive or thermally reactive groups, the coating agent can be exposed to a reaction energy source, such as light or thermal energy, to activate the latent reactive groups, thereby promoting formation of a coating on the substrate. A "reaction-energy source" is an energy source that promotes adherence of a molecule to a substrate, for example, by converting nitrenogenic groups on coating agent molecules to nitrenes, which may then react with the surface of a substrate. Suitable reaction-energy sources include (but are not limited to): photons, such as UV photons, and thermal energy (such as infrared radiation and conductive heating). Reaction-energy sources can be used alone or in combination. Reaction-energy sources are conventionally used for such tasks as lithography, scanning microscopy and, in the case of UV and visible photons, effecting photochemical reactions and excitation of fluorescent molecules. A reaction-energy source comprising UV light can be supplied, for example, using a mercury or xenon lamp. A medium pressure mercury lamp is a source of photons between about 220 nm and about 1,000 nm, with a maximal intensity at about 360 nm. A photomask may be used to prevent photons from reaching certain portions of a sample while allowing photons to reach other portions.

A thermal energy reaction-energy source can be supplied, for example, by heating a sample in an oven, typically ramped at a desired rate to a preselected working temperature or preheated to a designated temperature. In some embodiments, the designated temperature can be a temperature sufficient to increase the polymer chain mobility of the coating composition. The designated temperature can vary depending on the given polymer type. For example, the temperatures can be greater than the glass transition temperatures of the polymers being immobilized on the substrate, such as temperatures from about 120° C. to about 190° C., but less than ignition temperatures of the polymers.

The heating time can be a time sufficient to impart the necessary energy to bond the molecules to the substrate, such as between about 5 minutes and about 40 minutes.

In still further embodiments, the latent reactive groups can comprise chemical reactive groups. Suitable chemical reactive groups can be referred to as redox initiators, redox catalysis agents, or redox activation agents. In general, combinations of organic and inorganic oxidizers, and organic and inorganic reducing agents are used to generate radicals for polymerization. A description of redox initiation can be found in Principles of Polymerization, 2nd Edition, Odian G., John Wiley and Sons, pgs 201-204, (1981), that part which is herein incorporated by reference. Redox initiators that are not damaging to biological systems can be used in some embodiments.

Photoinitiator groups and thermally activated initiator groups that utilize energy that is not damaging to biological systems can also be used. In an embodiment, photoinitiator groups having long wavelength UV and visible light-activated frequencies are coupled to the backbone of the polymer. In other embodiments, visible light-activated photoinitiators can be pendent to the polymer.

In other embodiments the latent reactive groups of the compositions can include a photoreactive group, a chemically activated group, a thermal reactive group or combinations thereof.

After the coating agent has been applied to a substrate surface, the coating agent can be subjected to activation from a suitable source. This in turn forms a covalently bound coating on the substrate surface, the coating including the polymer having pendent "reacted" groups (such as photo- "reacted" or thermally "reacted" groups), meaning that photoreactive and/or thermally reactive groups have undergone activation to form a covalent bond, thereby immobilizing the polymer to the substrate surface. It is not required that all latent reactive groups be activated in order to covalently couple the coating to a substrate surface; some latent reactive groups may return to an inactive state upon removal of the activation energy.

In accordance with inventive aspects, the coating agents include a polymer, one or more latent reactive groups, and one or more non-covalent linking groups. Features of the polymer component will now be described.

As used herein, a "polymer" is a compound formed by covalently linking smaller molecules termed "monomers." The monomers present in a polymer molecule can be the same or different. If the monomers are different, the polymer also may be called a copolymer.

The polymer component of the coating composition can serve as a backbone for attachment of non-covalent linking groups, latent reactive groups, or both non-covalent linking groups and latent reactive groups. In these aspects, the non-covalent linking groups, the latent reactive groups, or both the non-covalent linking groups and the latent reactive groups can be described as being "pendent" from the polymer. Optionally, the polymer can serve as a backbone for attachment of active agents, as will be described in more detail elsewhere herein.

Generally, a non-covalent linking group that is "pendent" from the polymer is arranged on the polymer in a manner so that it can interact or associate with a substrate surface. The non-covalent linking groups can be pendent along the length of the polymer and spaced along the length of the polymer in a random or ordered manner. In accordance with these aspects, a polymer can be formed using any type of synthetic process that will result in the formation of a polymer with one or more pendent non-covalent linking groups. For example, a polymer can be synthesized by attaching non-covalent linking groups to a "preformed" polymer. The preformed polymer can be obtained from a commercial source or be synthesized from the polymerization of a desired monomer or combination of different monomers. In one example of preparing a polymer in accordance with these embodiments, a compound that includes a non-covalent linking group and a first reactive group is reacted with a portion of a polymer that is reactive with the first reactive group, resulting in the formation of a polymer having a pendent non-covalent linking group. The reaction preferably does not cause any modification to the non-covalent linking group that would interfere with its ability to interact with the substrate to be coated. Such attachments of the non-covalent linking group can be achieved by, for example, substitution or addition reactions. Alternatively, a polymer can be formed having pendent non-covalent linking groups by first preparing monomers that include the non-covalent linking groups, and then polymerizing the monomers to form a final polymeric coating agent. One of skill will readily appreciate the particular synthesis scheme can be selected depending upon the components of the coating agent and the final desired product. Both general synthesis schemes are illustrated in the Examples herein.

Similarly, a latent reactive group that is "pendent" from the polymer is arranged on the polymer in a manner so that it can be activated using the selected activation energy (such as light, thermal or other reaction condition) and bond to a substrate material to be coated. The latent reactive groups can be pendent along the length of the polymer and spaced along the length of the polymer in a random or ordered manner. A polymer in accordance with these embodiments can be formed using any type of synthetic process that will result in the formation of a polymer having one or more pendent latent reactive groups. For example, a polymer can be synthesized by attaching latent reactive groups to a "preformed" polymer. The preformed polymer can be obtained from a commercial source or be synthesized from the polymerization of a desired monomer or combination of different monomers. In one example of preparing polymer having pendent latent reactive groups, a compound that includes a photoreactive group and a first reactive group is reacted with a portion of a polymer that is reactive with the first reactive group, resulting in the formation of a polymer having a pendent photoreactive group. The reaction preferably does not result in the activation of the latent reactive group; therefore the latent reactive group remains "latent" and capable of activation by suitable activation energy during the coating process. Such attachments of the latent reactive group can be achieved by, for example, substitution or addition reactions. Alternatively, a polymer can be formed having pendent latent reactive groups by first preparing monomers that include the latent reactive groups, and then polymerizing the monomers to form a final polymeric coating agent. One of skill will readily appreciate the particular synthesis scheme can be selected depending upon the components of the coating agent and the final desired product.

In some embodiments, one or more of the non-covalent linking groups can be included within the polymer composition and backbone, as discussed in more detail elsewhere herein.

Suitable polymers may include polymeric entities such as oligomeric moieties, inorganic synthetic elastomers, block copolymers, linear polymers, linear copolymers, branched polymers, branched copolymers, homopolymers, natural polymers, positional isomeric polymers, stereo isomeric polymers and geometrical isomeric polymers.

In some embodiments the polymer can be a synthetic polymer such as vinyl polymers, polyolefins, sulfonic acid-substituted polymers, polyacrylamides, polyethylene glycols, polyethyleneimines, polylactic acids, polyglycolic acids, polylactide-co-glycolides, polyvinyl alcohols, polyvinyl pyrrolidones, quaternary amine-substituted polymers, silicones, silicone rubbers, conductive polymers (such as polyvinylpyridine, polyacetylene, polypyrrole), as well as derivatives, copolymers, or combinations of any of these.

In other embodiments the polymer can be alginic acid, cellulose, chitosan, glycogen, hyaluronic acid, pectin, monosaccharides, di-saccharides, starch, chitin, dextran sulfate, proteins, antithrombotic agents (such as antithrombin III and antithrombogenic surfaces), albumin, attachment proteins/peptides (such as collagen), enzymes, extracellular matrix proteins/peptides, growth factors, hirudin, thrombolytic proteins (such as streptokinase, plasmin, urokinase), as well as copolymers, combinations and derivatives of any of these.

In some embodiments, polymers include polymers prepared by radical polymerization, anionic polymerization, cationic polymerization, ring-opening polymerization, condensation polymerization or combinations thereof.

In some aspects, the polymer can include reactive groups. Such reactive groups can provide a reactive site on the polymer backbone for attachment of non-covalent linking groups, latent reactive groups and/or active groups. Such suitable reactive groups include, but are not limited to, carboxylic acid groups, glycidyl groups, anhydride groups, amine groups, acid chloride groups, acrylate groups, halogens, alkene groups, alkyne groups, hydroxyl groups, aldehyde groups, thiol groups, azide groups and mixtures thereof. In one illustrative embodiment, the polymer can be poly(maleic anhydride-alt-1-octadecene). Other suitable reactive groups include benzophenone and azo groups. In accordance with embodiments where the polymer includes reactive groups, such reactive groups can provide a reactive site for attachment of components to the polymer backbone (such as non-covalent linking groups, latent reactive groups, active groups, and the like). The resulting polymer would include such components as pendent groups from the polymer backbone, as described herein.

While the polymers can include a variety of polymeric moieties as described above, some embodiments include polymers with number average molecular weights (Me) in the range from about 500 to about 2,000,000. Other embodiments include polymers with number average molecular weights ($M_n$) in the range from about 1,000 to about 20,000, from about 10,000 to about 20,000, from about 20,000 to about 30,000, from about 30,000 to about 80,000, from about 80,000 to about 100,000, from about 100,000 to about 200,000, from about 200,000 to about 500,000, from about 500,000 to about 1,000,000 and even polymers with number average molecular weights ($M_n$) in the range from about 500,000 to about 2,000,000.

Additionally, for embodiments where a solution of the coating agent is applied to the substrate, polymers in the solubility range from about 0.01 mg/ml to about 2,000 mg/ml can be useful. In other applications, polymers in the solubility range of from about 0.10 mg/ml to about 2,000 mg/ml, from about 1.0 mg/ml to about 1,000 mg/ml, from about 10 mg; ml to about 2,000 mg/ml, from about 100 mg/ml to about 2,000 mg/ml or even in the range from about 1,000 mg/ml to about 2,000 mg/ml can be useful.

One of skill in the art will readily appreciate that the coating agents described herein can be modified to include additional components, if desired. For example, coating agents can optionally include one or more active agents. Such active agents can be selected to provide additional features or properties to the coating agent and/or a surface to which the coating agent is applied. The one or more active agents can be pendent from the polymer. When pendent from the polymer, active agents can be attached to the polymer backbone via reactive groups, as mentioned elsewhere herein.

Illustrative active agents include, but are not limited to, initiator groups, passivating groups, and chemical moieties that provide one or more desirable features to the coating agent, such as anti-microbial, anti-fouling, anti-angiogenic, angiogenic, antifibrotic, fibrotic, anti-thrombotis and/or protein resistant features.

In some embodiments, the active agent can comprise initiator groups. In these aspects, initiator groups can be used to initiate polymerization from a surface of a substrate. When an initiator group is included, polymerization can be performed from the surface of a substrate coated with the coating composition. In some aspects, the initiator groups can be used to form a polymer brush coating on the substrate surface.

Thus, in some aspects, there is provided a method for forming a coating on a surface of a substrate, the method comprising applying a coating agent to a substrate surface, the coating agent comprising: (a) polymer, (b) one or more latent reactive groups, (c) one or more noncovalent linking groups, and (d) one or more active agents. The active agents can comprise initiator groups. After application of the coating agent, the substrate surface is subjected to reaction conditions to form a brush polymer on a surface. Accordingly, a monomer composition is applied to the coated composition, and polymerization is conducted at the surface, to provide a polymer brush coating on the surface.

As used herein, a "polymer brush coating" refers to a polymeric chain that is formed from a polymerizable substrate having a radical-generating group (the initiator group of the coating composition), wherein the polymerizable substrate is the coated composition on the substrate. The polymer brush coating thereby substantially takes the form of the coated composition on the substrate surface. Polymer brushes are formed by radical polymerization as described herein. A brush has an elongated shape of a particular size in one direction related to the degree of polymerization in a first direction, its "length," and a cross sectional diameter or thickness is related to the degree of polymerization in a second direction perpendicular to the first direction, its "width." The brushes can assume a coiled or compacted morphology or an extended morphology. The width of a brush can vary along its length. In addition, the polymerization reaction can be controlled to create branchlike polymer brush structures, as well as increasing or decreasing brush density, that is, number of brushes per surface area or per weight of base material. The length, width, branching and overall morphology of the polymer brushes in accordance with inventive principles can be varied according to the desired end use or purpose as described herein and by methods known in the art.

Selection of an initiator group can take into account the type of polymerization to be performed. For example, benzophenone or azobisisobutyronitrile (AIBN) can be included in a coating agent, for use as a polymerization initiator. In these instances, polymerization is initiated upon application of a suitable activation energy (light energy in the case of benzophenone, and thermal energy—heat—in the case of AIBN), when the initiator decomposes into free radicals.

Controlled polymerization techniques based on free radical, anionic, cationic, ring opening and ring-opening metathesis polymerizations have been used to initiate polymerization for producing brush type polymers. In addition, free radical generators, such as benzophenones or azides, initiate polymerization of monomers to produce brush polymers with actinic activation (in the case of benzophenones) or with thermal activation (in the case of azides). All of the strategies include specialized initiator groups and these groups can be incorporated into the coating agent. The initiator groups provide a site for reaction with monomers to produce covalently attached polymeric units by "grafting from" technique or, alternatively, for reaction with prefabricated polymers by a "grafting to" technique. The attachment of polymers to the coating agent through controlled polymerization techniques allows for additional functionalization of the coating agent to achieve various surface properties. For example surfaces can be anti-microbial, anti-fouling, anti-angiogenic, angiogenic, anti-fibrotic, fibrotic, anti-thrombotic and protein resistant by functionalization with the chemical moiety known to serve this purpose. The functionalization of the coating agent activated by the initiator group can be completed either before or after application of the coating agent to the substrate.

Radical based strategies include atom transfer radical polymerization (ATRP), reversible-addition fragmentation chain transfer (RAFT), nitroxide-mediated polymerization (NMP) and photoiniferter-mediated polymerization. (See Chem. Rev. 2009, 109, 5437-5527 for review of surface-initiated controlled radical polymerization). ATRP relies on the reversible redox activation of a dormant alkyl halide initiator group, such as bromoisobutyrate, and the propagation of the polymer chain is based on reversible termination. RAFT is base on reversible chain transfer and relies on activation of either conventional free-radical initiators in the presence of a chain transfer agent, such as 2-phenylprop-2yl dithiobenzoate, or RAFT agents such as dithiobenzoate or trithiocarbonate. NMP relies on reversible activation/deactivation of growing polymer chains by a nitroxide radical which can be activated by 2,2,2,6,6-tetramethyl piperidinyloxy (TEMPO).

"Polymerizable monomer" refers to a polymerizable allylic, vinylic, methacrylic or acrylic compound. In some aspects, the monomer is zwitterionic. "Zwitterionic monomer" means a polymerizable molecule containing cationic and anionic (charged) functionality in equal proportions, so that the molecule is not neutral overall.

Representative zwitterionic monomers include N,N-dimethyl-N-acryloyloxyethyl-N-(3-sulfopropyl)-ammonium betaine, N,N-dimethyl-N-methacryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, N,N-dimethyl-N-acrylamidopropyl-N-(3-sulfopropyl)-ammonium betaine, N,N-dimethyl-N-methacrylamidopropyl-N-(3-sulfopropyl)-ammonium betaine (SBMAM), N,N-dimethyl-N-acrylamidopropyl-N-(2-carboxymethyl)-ammonium betaine, N,N-dimethyl-N-methacrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2'-(trimethylammonium)ethyl phosphate. [(2-acryloylethyl) dimethylammonio]methyl phosphonic acid, 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N,N-diallylamine ammonium betaine (MDABS), or $N_5$N-diallyl-N-methyl-N-(2-sulfoethyl) ammonium betaine, 2-methacryloyloxyethyl phosphorylcholine, and the like.

In accordance with inventive principles, ATRP can be used. As discussed abive, ATRP is a controlled or "living" polymerization based upon the use of radical polymerization to convert monomer to polymer. Carbon-carbon bonds are formed through a transition metal.

Using ATRP as an example, suitable initiator groups include organic halides that are similar in the organic framework as the propagating radical. Illustrative initiator groups are alkyl halides. In some embodiments, the initiator group comprises an alkyl bromide. Illustrative initiator groups include bromoisobutyrate. Other ATRP initiators are commercially available, for example, from ATRP Solutions (Pittsburgh, Pa.). The polymerization catalyst can be a suitable metal catalyst. In some aspects, the catalyst can provide a beneficial combination of the following: two accessible oxidation states that are separated by one electron, suitable affinity of the metal center for halogens, expandability of the coordination sphere of the metal when it is oxidized to allow the metal to accommodate the halogen, and a strong ligand complexation. Illustrative catalysts are copper-based. Monomers typically used in ATRP are molecules with substituents that can stabilize the propagating radicals, for example, styrenes, (meth)acrylates, (meth)acrylamides, and acrylonitrile. Illustrative solvents for atom transfer radical polymerization include toluene, 1,4-dioxane, xylene, anisole and water.

In accordance with these aspects, a substrate can be provided with a coating agent, and atom transfer radical polymerization can be initiated from the coated substrate, to thereby form a brush polymer coating on the substrate surface. A substrate is immersed in a coating composition containing the coating agent (polymer, latent reactive group, noncovalent linking group and initiator) for a suitable time and then dried to remove remaining solvent. Subsequently, the coated substrate is immersed in a coating composition containing a zwitterionic monomer (such as SBMAm) and degassed under argon.

It will be appreciated that selection of initiator to include in a coating agent may also take into account the noncovalent linking group(s) of the coating agent. The initiator can be the same as, or different from, the noncovalent linking group selected. For example, benzophenone can be included as part of the coating agent, and serve as both an initiator and as a latent reactive group. In these instances, the coating agent can be applied to a surface, activating energy can be applied to couple the coating agent to the surface, under conditions such the less than all of the benzophenone groups are activated. Unreacted benzophenone groups can then return to the latent state, and subsequently be used as initiators for polymerization.

In other instances, the noncovalent linking group and initiator can be different. For example, when benzophenone is used as a non-covalent linking group, other free radical generating moieties may be used to provide free radicals to initiate polymerization. For example, when benzophenone is included as a noncovalent linking group of the coating agent, it can be desirable to select an initiator that is not benzophenone, such as a diazo compound. This can be advantageous, for example, in conditions where light is available to achieve crosslinking of the coating with benzophenone by actinic activation but allows diazo compounds to thermally initiate polymerization in the dark.

Other suitable active agents can be selected to provide protein and microbial passivating properties. In accordance with these aspects, illustrative active agents can be selected from carboxylate ($COO^-$), sulfate ($SO_3^-$), hydroxy ($OH^-$), amine ($NH_2$), methyl ($CH_3$), polyethylene glycol (PEG), siloxyl (SiO), or perfluoro [$(CF_3)_n$—$CF_3$)] groups. In one embodiment the PEG active agent can comprise methoxy-polyethylene glycol amine (Aldrich Chemical Company, WI). An illustrative perfluoro agent agent is 1H, 1H-pentadecafluoroctylamine (available from Oakwood Chemical, CA).

Coatings are applied as described herein. If desired, coated substrates can be heated to a suitable temperature for a suitable time (for example, 140° C. for 5 to 30 minutes) to crosslink the coating.

As discussed herein, coating agents can include a combination of the following components associated with the polymer: noncovalent linking group, latent reactive group, and/or active agents. Each of these components of the coating agent can be provided to the polymer either before or after the polymer is formed. For example, monomers can be modified to include the desired component. These modified monomers can then be polymerized to form a final polymer containing the selected components. Alternatively, a polymer can first be formed (a "preformed" polymer), and desired components can be coupled to the polymer subsequently.

In accordance with inventive principles, components (noncovalent linking group(s), latent reactive group(s) and/or active agent(s)) can be coupled to the polymer using suitable reaction conditions. As illustrated in the Examples, active agents can be reacted with maleic anhydride monomers to form stable amide bonds. The resulting modified monomers are negatively charged, as the reaction of each maleic anhydride unit with an active agent generates a free carboxylate group. Alternatively, and as also illustrated in the Examples, preformed polymers can include reactive groups (such as maleic anhydride), and components (non-covalent linking group(s), latent reactive group(s) and/or active agent(s)) can be reacted with the maleic anhydride groups on the polymer to form stable amide bonds. One of skill will readily appreciate that other reactive groups can be substituted for maleic anydride in accordance with teachings herein.

Embodiments of the invention include methods for depositing a coating agent and forming a coating on a substrate. In some embodiments of the invention, the coating includes a coating agent including a polymer, a latent reactive group, and a non-covalent linking group. The latent reactive group and the non-covalent linking group can be different from each other. The non-covalent linking group is selected to interact with a substrate to which the coating agent is applied.

As a preliminary step, the substrate surface can optionally be cleaned and prepared so that the coating agent can properly bind to the substrate. By way of example, contaminants that may interfere with binding of the coating agent can be removed by wiping, dipping or combinations thereof of the substrate with a solvent (such as, for example, isopropyl alcohol). Optionally, the substrate surface may also be treated with agents so that the substrate surface will have oxide or hydroxyl groups disposed thereon. For example, the substrate can be treated with a strong base such as sodium hydroxide, ammonium hydroxide, and the like. In the case of a metal, the metal can be subjected to an oxidizing potential to generate oxide or hydroxide sites on the surface of the metal.

In embodiments where the coating agent can be formed with a polymer, a latent reactive group, and a non-covalent linking group, the individual components of the composition can be mixed together in a suitable solvent to form a coating composition. In these embodiments, polymer, latent reactive group and non-covalent linking group coating composition can be applied to the substrate at the same time as a part of the same composition. Alternatively, a polymer, a latent reactive group and a non-covalent linking group can be separately prepared and applied to the substrate to be coated. One will appreciate that different types of polymers, latent reactive groups, and non-covalent linking groups can be combined to arrive at desired end points of coated substrate surfaces. Such desired endpoints include, but are not limited to lubricity, hydrophilicity, hydrophobicity, adhesion, durability, biocompatibility, texture and combinations thereof.

In some embodiments, the polymer can include oligomeric moieties, inorganic synthetic elastomers, block copolymers, linear polymers, linear copolymers, branched polymers, branched copolymers, homopolymers, natural polymers, positional isomeric polymers, stereo isomeric polymers, and geometrical isomeric polymers in combinations or blends. In an embodiment, the polymer can include a copolymer. In an embodiment, the copolymer includes octadecene and a maleic acid derivative.

In an embodiment, the latent reactive group can include a photoreactive or thermally reactive moiety. Suitable photoreactive moieties include azides, diazos, diazirines, ketones, and quinones. Suitable thermally reactive moieties can include 4,4' azobis(4-cyanopentanoic acid) and analogs of benzoyl peroxide. In an embodiment, the photoreactive group can include acetophenone, anthrone, including acridone, benzophenone, xanthone, thioxanthone, or their ring substituted derivatives, or a quinone such as, for example anthraquinone. In an embodiment the photoreactive moiety can include benzophenone.

In some embodiments the non-covalent linking group can include siloxane groups, dopamine, $C_4$-$C_{20}$ alkyl groups, polyethylene glycol, and polyethylene glycol, acrylates, polyacrylates, polyurethanes, polycarbonates, polyesters, polyethylenes, polypropylenes and polyethers, or the like. In other embodiments, a coating layer can be formed from reacting components of the polymer, the latent reactive group and the non-covalent linking group to produce the coating agent for application to a silicon-containing substrate. In an embodiment the non-covalent linking group includes a siloxane. In an embodiment the non-covalent linking group is a reaction product including 3-aminopropylmethylbis(trimethylsiloxy)silane.

In an embodiment, the polymer, and the latent reactive group are mixed together using appropriate reaction conditions and solvents for the components. After reacting the polymer and latent reactive components, the non-covalent linking group component is added to the reaction mixture to produce the coating agent including pendent non-covalent linking group(s) and latent reactive group(s). A suitable composition includes reacting 3-aminopropylmethylbis(trimethylsiloxy)silane, poly(octadecene-alt-maleic anhydride) and benzophenone to make a polymeric coating agent with a pendant siloxane group as represented in Formulae (I) and (IV). The resultant coating agent may be applied to a PDMS surface wherein treatment with actinic energy, such as UV-light, occurs and the surface coating composition is covalently attached to PDMS surface. After treatment with actinic energy, additional coating layers may be applied, optionally, to the coating layer to provide additional surface modification.

In some embodiments a coating composition can be formed. The coating composition can be applied to the substrate from a solvent. Suitable solvents include isopropyl alcohol, ketones, alkanes, chloroform, alcohols, tetrahydrofuran (THF), ethyl acetates, methyl acetates, water, dioxanes, ethers, toluene, petroleum ethers, and mixtures thereof. Different types of application techniques can be used to apply the coating composition to the surface of the substrate. By way of example, but not intended to be limiting, one can appreciate that the coating composition can be sprayed onto the surface of the substrate, dip-coated onto the surface of the substrate, wiped onto the surface of the substrate, blade-coated onto the surface of the substrate, sponge coated onto the surface of the substrate, or combinations thereof. The substrate with the coating composition can be exposed to actinic energy, for example UV-light, to induce reaction of the latent reactive group with the substrate. After exposure to actinic energy, the coated substrate can be washed to remove any unbound (for example, non-covalently bound) materials.

Alternatively, it will be appreciated that the non-covalent linking group, the polymer and the latent reactive groups can be applied as separate compositions to the substrate to be coated. Therefore, after a sufficient time to allow reaction of the composition, external energy can be applied to bond the layer to the substrate. A wash step can be performed to remove unbonded materials. In this embodiment, a latent reactive agent can then be applied separately to the substrate. However, in either embodiment the latent reactive agent will retain reactive groups that are available for further reaction, for example, to couple to a hydrophobic polymer layer or other moieties as is appropriate.

Optionally, such as when the coating agent is intended to serve as a primer, an active agent layer can be disposed over the surface primer coated layer. By way of example, an active agent layer composition can be prepared by mixing one or more polymers together with an active agent in an appropriate solvent. The active agent layer can then be applied to the surface primer coated layer through any suitable technique including spray coating, dip coating, blade coating, and the like.

In still further embodiments, a passivating coating can be applied as an overcoat. For example, a coating agent (including polymer, latent reactive groups and noncovalent linking groups) can be applied to a substrate as a primer. In some embodiments, the latent reactive groups of the primer coating agent can comprise thermally reactive groups. Subsequent to application of a primer coating agent, a passivator overcoat composition can be applied. The passivator overcoat composition can comprise polymer and latent reactive groups. In some embodiments, a noncovalent linking group is not included in the passivator overcoat composition.

In some embodiments surface modified articles include devices that can be inserted into the body of a mammal. Such articles include, but are not limited to, vascular devices such as guidewires, stents, stent grafts, covered stents, catheters, valves, distal protection devices, aneurysm occlusion devices, septal defect closures and artificial hearts; heart assist devices such as defibrillators, pacemakers and pacing leads; orthopedic devices such as joint implants and fracture repair devices; dental devices such as dental implants and fracture repair devices; ophthalmic devices and glaucoma drain shunts; urological devices such as penile, sphincter, urethral, bladder and renal devices; and synthetic prostheses such as breast prostheses and artificial organs. Coating layers on medical devices are durable and well suited to applications in which the medical device is subjected to twisting and bending during insertion into a patient, and/or during residence of the device within a patient.

Other embodiments of inorganic substrate include non-implanted biomedical devices such as, but are not limited to, diagnostic slides such as gene chips, DNA chip arrays, microarrays, protein chips, and fluorescence in situ hybridization (FISH) slides; arrays including cDNA arrays, and oligonucleotide arrays; chromatographic support materials, cell culture devices, biosensors, and the like.

In alternative embodiments, the surface modified articles described above can include a substrate; a coated layer including (a) a polymer, (b) at least one latent reactive group, (c) at least one non-covalent linking group, and (d) at least one overcoat layer.

The overcoat layer can be a hydrophilic polymer. The hydrophilic polymer can include synthetic polymers, natural polymers, polyionic polymers or a combination thereof. The hydrophilic polymer can be a copolymer or a homopolymer. Suitable natural hydrophilic polymers include alginic acid, alginate, heparin, hyaluronic, acid, hyaluronate, polylysine, saccharide, chitosan, dextran, gelatin, collagen, cellulose, keratin, polypeptide, nucleotide, protein, and the like. Suitable synthetic hydrophilic polymers can be prepared from acrylic monomers, vinyl monomers, ether monomers, or combinations thereof. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives thereof. Vinyl monomers include, for example, vinyl acetate, vinyl pyrrolidone, vinyl alcohol, and derivatives thereof. Ether monomers include, for example, ethylene oxide, propylene oxide, butylene oxide, and derivatives thereof. Polyionic monomers include, for example, quaternary ammonium, ethyleneimine, or combinations thereof.

Suitable hydrophilic polymers can include copolymers such as, for example, polymethyl vinyl ether/maleic anhydride copolymers, polyvinyl pyrrolidone/polymethacrylamide copolymers, and polyvinyl pyrrolidone/polyacrylamide copolymers.

In some aspects, the overcoat layer can be a hydrophobic polymer. Optionally, the overcoat layer can be a superhydrophobic polymer or an ultrahydrophobic polymer. Illustrative superhydrophobic and ultrahydrophobic polymers are described in commonly owned United States Patent Publication Numbers 2010/0081750 A1 (published Apr. 1, 2010; Guire, et al., "Nanotextured Surfaces") and 2008/0268233 (published Oct. 30, 2008; Lawin, et al., "Nanotextured Super or Ultra Hydrophobic Coatings").

It can be desirable to have more than one overcoat layers on a coated primer layer. For example, a lubricious coating layer can be combined with a drug-release layer to provide a surface modified article with a lubricious surface and a specific drug-release profile. In yet other examples, surface modified articles can provide durable antimicrobial activity.

In some embodiments of the present invention, the overcoated article (for example, the article including a substrate, primer layer and overcoat) can be subjected to actinic energy providing further beneficial surface modification to the article. For example, subjecting the overcoated article to actinic radiation can, in some cases, increase the durability of the surface modified article in use.

One of skill will appreciate the inventive concepts can be applied to provide improved features to a variety of substrates that would otherwise be difficult to coat with conventional techniques. For example, in some embodiments, articles are described comprising a substrate comprising a polyolefin, and a coating disposed on a surface of the substrate, the coating comprising: (a) a polymer backbone, (b) one or more latent reactive groups that are pendent from the polymer backbone, and (c) one or more noncovalent linking groups, the noncovalent linking groups selected to interact with the substrate. The substrate can comprise polyethyelene. The noncovalent linking group can be a catechol.

In still further aspects, articles are provided that comprise a substrate fabricated of a metal, and a coating disposed on a surface of the substrate, the coating comprising: (a) a polymer backbone, (b) one or more latent reactive groups that are pendent from the polymer backbone, and (c) one or more noncovalent linking groups, the noncovalent linking groups selected to interact with the substrate. The metal can be one or more of stainless steel, aluminum, nitinol or cobalt-chromium. The noncovalent linking group can comprise a siloxane.

The following examples are representative of embodiments of the present invention and not intended to be exhaustive. The examples are not to be taken as limiting the scope of the invention but rather so that others skilled in the art can appreciate practices of the present invention. Unless otherwise noted, all percentages are by weight.

EXAMPLES

The following reagents were utilized in the Examples. Lubricent™: Hydrophilic coatings consisting of a blend of a hydrogel-forming polymer combined with a photoreactive compound dissolved in isopropyl alcohol, commercially available under the product name Lubricent™ 460, from Harland Medical, Eden Prairie, Minn.

Example 1

Synthesis of Photo-Poly(octadecene-alt-maleic anhydride)silane—(Photo-POMAS)

Five grams of poly(octadecene-alt-maleic anhydride), (MW 30,000-50,000, Aldrich, Milwaukee, Wis.), 0.5 g of 4-aminobenzophenone (Aldrich) and 0.08 g 4-dimethylaminopyridine (Aldrich) were dissolved in 100 mL chloroform and refluxed under argon for 2 hours. A 5 ml aminopropyl methylbis(trimethylsiloxy)silane portion was then added to the reaction mixture and refluxed for another 2 hours. The resulting solution was washed three times with 2N HCl, followed by three washes with deionized water. The sample was dried over anhydrous $Na_2SO_4$. After vacuum filtration, the filtrate was concentrated to dryness on a rotavap to yield 7.5 g of solid material.

The polymer product was characterized by $^1H$ NMR (δ 0.0 ppm, C$\underline{H}_3$—Si; δ 0.8-1.5 ppm, alkyl protons; δ 2.5-3.5 ppm, C$\underline{H}$—C=O; δ 7.4-7.6 ppm, aromatic protons) and FT-IR (C=O: 1710 cm$^{-1}$; benzophenone: 1593 cm$^{-1}$; Si—CH$_3$: 1258 cm$^{-1}$, 843 cm$^{-1}$, 755 cm$^{-1}$; Si—O—Si: 1052 cm$^{-1}$). The polymer product was soluble in common solvents including isopropanol (IPA), acetone, hexane, chloroform, tetrahydrofuran (THF), and ethyl acetate, but insoluble in water. The polymer product had the structure represented by Formula IV below, where the "noncovalent linking group" is siloxane.

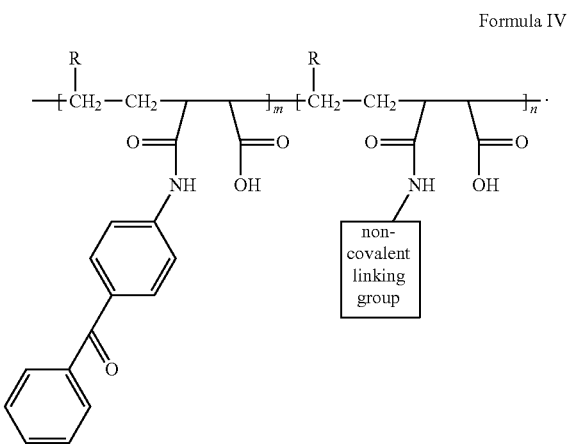

Formula IV

Example 2

Coating of Silicone Tubing with Photo-POMAS

A 7.5 g amount of the Photo-POMAS polymer, prepared as previously described in Example 1, was dissolved in 100 ml of IPA. Five pieces of 10 cm silicone tubing (DOVER™ silicone catheter, Covidien) were prepared for coating with the polymer by cleaning with a brief hand-rub of isopropanol. The silicone tubing pieces were coated with the Photo-POMAS/IPA solution by immersing the pieces in the solution for 30 seconds, then extracting the pieces of tubing from the coating solution at 0.5 cm/sec. The pieces were air dried at room temperature for 3 minutes, then irradiated with ultraviolet light (Harland Medical UVM400, Eden Prairie, Minn.) (300 to 400 nm) for 1 minute at a distance of 15 cm from the light source.

The photo-POMAS coating on the silicone tubing was characterized by SEM and Confocal Raman Microscope (FIG. 1). A uniform coating was confirmed. In FIG. 1, confocal Raman microscopy revealed a uniform coating on silicone catheter (red, silicone; green, primer coating; blue, additive in silicone rubber).

Example 3

Lubricious Coating

The Photo-POMAS coated tubing pieces prepared in Example 2 were coated with Lubricent™ 460 by immersing the Photo-POMAS coated pieces in a Lubricent™ solution for 30 seconds, then extracting the Photo-POMAS and Lubricent™ coated silicone tubing at 0.5 cm/sec. The coated silicone pieces were air dried at room temperature for 3 minutes, then irradiated with ultraviolet light (300 to 400 nm) at 15 cm for 3 minutes. Silicone tubing coated with Lubricent™ without the Photo-POMAS polymer primer coating layer was used as a control.

Example 4

Congo Red Staining

Congo red was used to detect the presence of the Lubricent™ coating on the surface of the silicone tubing, prepared as described in Example 3. Lubricent™ coatings with a Photo-POMAS polymer primer coating layer and without a Photo-POMAS polymer primer coating layer were rinsed with deionized water extensively and then immersed into 50 mg/ml Congo red solution (Aldrich Chemicals, Milwaukee, Wis.). After 1 minute of soaking in the Congo red solution, the samples were removed and rinsed with deionized water 3 times.

The coating of silicone tubing samples containing a Photo-POMAS polymer primer layer was stained visibly red, while the coating without the Photo-POMAS coating primer layer did not show a visible red stain. The visible indication of Congo red in the coating layer showed only silicone tubing that included a Photo-POMAS polymer primer coating layer retained a coating of Lubricent™. Results also demonstrated a uniform coating on coated silicone catheter.

Example 5

Friction Test

The coated silicone pieces prepared as described in Example 3 above (coatings including Photo-POMAS and Lubricent™) were tested with a commercial friction tester (Harland Medical, FTS 5000, Eden Prairie, Minn.) for lubricity. In this test, the coated tubing pieces were hydrated for 2 minutes in deionized water and then the silicone pads of the friction tester were compressed against the tubing while the tubing was immersed in water. The tubing piece was pulled upward at the rate of 1.0 cm/sec for a distance 6.0 cm. After testing, the clamps were released and the tubing piece moved freely downward 6.0 cm at 2.0 cm/sec. This friction testing cycle was repeated fifteen times.

Figure 2:
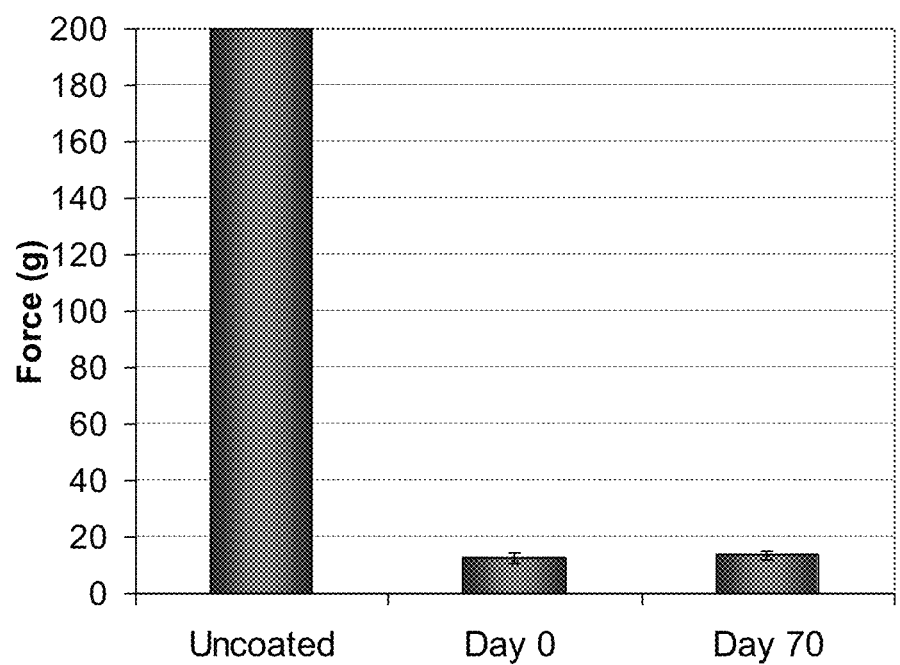
FIG. 2 illustrates results of friction testing on silicone catheters coated with coating agent followed by a lubricious overcoat.

The average friction force required to pull the Photo-POMAS and Lubricent™ coated silicone tubing through the silicone pads with 300 g of force on the tubing piece was approximately 10 g. The average friction force to pull tubing without the primer coating but with the Lubricent™ coating through the silicone pads exceeded 250 g. No significant change from the 10 g of force required for the Photo-POMAS and Lubricent™ coated silicone tubing was seen throughout the fifteen cycles of the friction test. The friction test was performed again on the coated samples after being stored at room temperature for 70 days (FIG. 2).

Example 6

Superhydrophobic Coating

Silicone tubing pieces were coated with Photo-POMAS as described in Example 2. After a period of 40 days, the silicone tubing pieces were coated with a superhydrophobic coating composition as follows.

A superhydrophobic coating composition consisting of 16 mg/ml fumed silica particles (commercially available under the product name CAB-O-SIL TS720, Cabot Corporation, Boston Mass.) and 13.3 mg/ml polyisobutylene (PIB) (BASF, Florham Park, N.J., MW 2000K) in hexane was prepared. Silicone tubing pieces were coated with the superhydrophobic coating composition by immersing the Photo-POMAS coated pieces in the superhydrophobic coating composition for 30 seconds, then extracting the tubing at 0.5 cm/sec. The coated silicone pieces were air dried at room temperature. Water wettability was investigated by immersing the coated pieces in water.

Figures 3A, 3B:
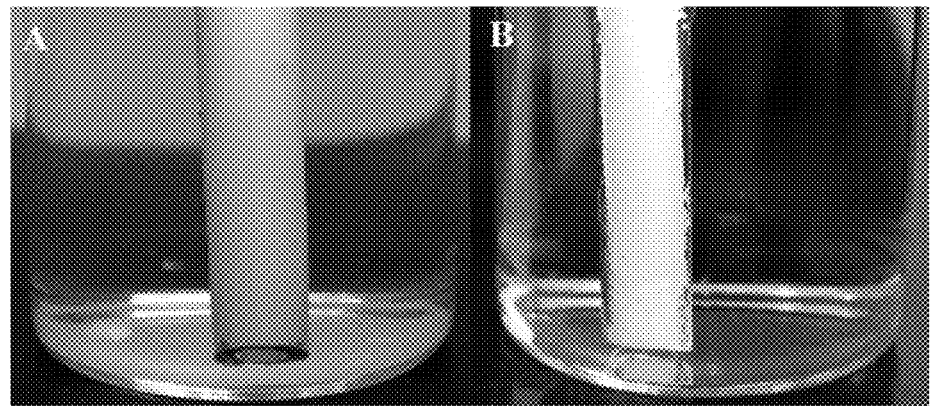
FIG. 3A shows a superhydrophobic overcoat applied on unprimed catheter.
FIG. 3B shows a superhydrophobic overcoat applied on a catheter including a surface primer agent.

Results are shown in FIG. 3, which illustrates that the superhydrophobic coating only adhered to the silicone pieces that included a Photo-POMAS coating layer, whereas the unprimed pieces (those pieces that did not include a Photo-POMAS coating) were not superhydrophobic even though superhydrophobic formulation had been applied. In FIG. 3A, a superhydrophobic coating applied on unprimed catheter does not show a superhydrophobic effect in water. In contrast, in FIG. 3B, a superhydrophobic coating applied on primed catheter does not wet and retains a layer of trapped air.

Example 7

Cytotoxicity

Samples of silicone tubing (0.9 cm diameter, 8 cm long) were cleaned with a brief hand-rub of isopropanol and coated with 30 mg/ml Photo-POMAS/IPA solution (prepared as described in Example 1) by immersing the pieces in the solution for 30 seconds, then extracting the pieces from the coating solution at 0.5 cm/sec. The pieces were air dried at room temperature for 3 minutes, then irradiated with ultraviolet light (Harland Medical UVM400, Eden Prairie, Minn.) (300 to 400 nm) for 2 minutes at a distance of 15 cm from the light source.

Figure 4:
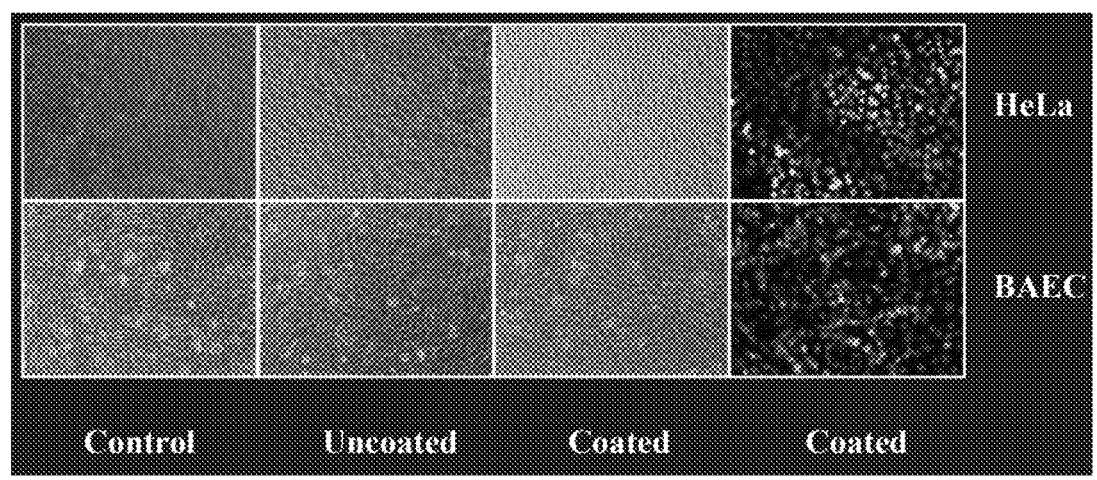
FIG. 4 shows results of cytotoxicity studies for silicone samples with and without treatment of a coating agent.

For a cytotoxicity study, 3.5 cm long coated and uncoated samples were then UV sterilized for 10 minutes. Each sample was incubated with 6.5 ml DMEM-10%/o FBS containing Pen-Strep (Invitrogen. Carlsbad, Calif.) at 37° C. overnight. 1 ml of the extract medium was added to each well of 24-well plate preseeded with HeLa or BAEC cells. The cell growth and morphology were monitored by observing under microscope and a live/dead assay was performed on day 3. Results indicated that the Photo-POMAS coating was non-cytotoxic, as illustrated in FIG. 4.

Example 8

Photopatterning

Selective application of coating agent on a substrate was demonstrated by applying a Photo-POMAS coating and subsequently exposing the coating to activation energy in conjunction with a mask as follows. The substrates for this example comprised silicone discs (1.2 cm, prepared as described in Example 16). Prior to application of the coating, the silicone discs were cleaned by immersion in isopropyl alcohol (IPA), followed by sonication for 15 minutes. The discs were then placed on a rocker for 5 minutes.

Figure 5:
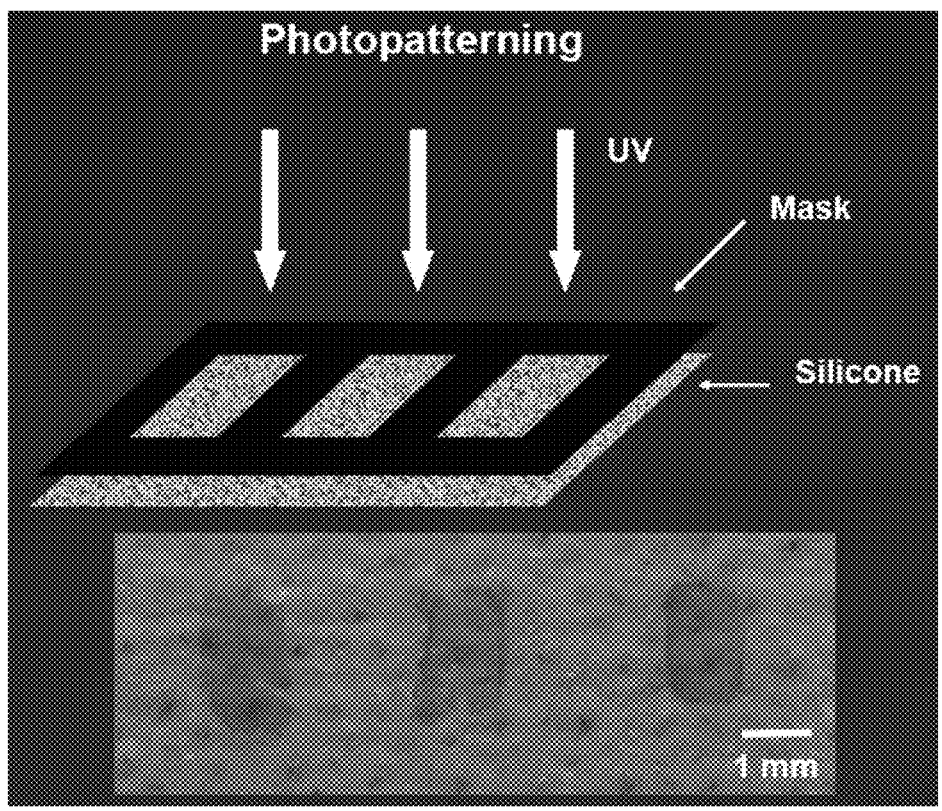
FIG. 5 illustrates photopatterning of a hydrophilic overcoat, applied to a silicone surface containing a surface primer agent.

Next, the entire surface of each silicone disc was coated with Photo-POMAS coating as described in Example 2 and air dried at room temperature for 3 minutes. The silicone discs were then irradiated with ultraviolet light (Harland Medical UVM400, Eden Prairie, Minn.) (300 to 400 nm) through a mask for 1 minute at a distance of 15 cm from the light source, as illustrated in FIG. 5. Next, the coated samples were sonicated in IPA for 2 minutes. Subsequent to sonication, a hydrophilic coating was then applied to entire surface of each disc as described in Example 3. The coated samples were extensively rinsed with water by gentle rubbing and stained with Congo red. FIG. 5 shows that the hydrophilic coating only adhered to the regions with UV exposure (as shown by staining in red).

Example 9

Coating Stainless Steel with Photo-POMAS

A 30 mg/mL solution of Photo-POMAS in isopropanol was prepared as previously described. A stainless steel substrate was prepared for coating with the polymer by cleaning with isopropanol. The cleaned substrate was then coated with the Photo-POMAS/IPA solution by immersing the substrate in the solution for 30 seconds, then extracting the substrate from the coating solution at 0.5 cm/second. The sample was then air dried at room temperature, then irradiated with ultraviolet light (Harland Medical UVM400. Eden Prairie, Minn.) (300-400 nm) for 1 minute at a distance of 15 cm from the light source.

The Photo-POMAS coated stainless steel piece was coated with Lubricent™ by immersing the Photo-POMAS coated pieces in a Lubricent™ solution for 30 seconds, then extracting the Lubricent™ coated substrate at 1 cm/second. The coated substrate was air dried at room temperature for 10 minutes, then irradiated with ultraviolet light (Harland Medical UVM400. Eden Prairie, Minn.) (300-400 nm), for 5 minutes at a distance of 15 cm from the light source. The sample was rinsed with deionized water with gentle rubbing.

The coated sample was dipped in Congo red stain for the presence of the coating as previously described in Example 4. The spotty presence of Congo red staining in the coating layer showed stainless steel primed with Photo-POMAS partially retained a coating of Lubricent™.

Example 10

Synthesis of Poly(1-octadecene-at-maleic anhydride)benzophenone (POMA-BP)

A 5.0173 g amount of poly(maleic anhydride-alt-1-octadecene) (POMA) was added to a 250 round-bottomed one-neck flask equipped with a stir bar and reflux condenser. A 4.0720 g amount of 4-aminobenzophenone (BP), 0.0896 g of 4-(dimethylaminopyridine) and 100 ml of chloroform (Fisher Chemicals, Pittsburgh, Pa.) were then added to the flask and stirred. The reaction was stirred and refluxed at 83° C. in an oil bath for 2 hours with argon, and the solvent was removed with a rotary evaporator.

The residue was dissolved in 50 mL chloroform and was washed three times with 50 ml of 1N hydrochloric acid and three times with 50 ml of deionized water. The organic layer was dried over sodium sulfate, filtered and concentrated to dryness as described in Example 1. The dried solid had a bright yellow color.

Example 11

Coating Silicone with POMA-BP

A 10 cm piece of silicone tubing was cleaned with isopropanol and dried. The silicone tubing piece was dipped into a coating solution including 60 mg/mL POMA-BP (prepared as described in Example 10) in isopropanol at a speed of 1 cm/sec with a dwelling time of 30 seconds. The tubing was extracted from the coating solution, dried and illuminated under a UVM 400 ultraviolet lamp for 1 minute at a distance of 15 cm.

The POMA-BP coated silicone tubing piece was dipped into a coating solution of Lubricent™ at a speed of 1 cm/sec with a dwelling time of 30 seconds, and then illuminated under a UVM 400 ultraviolet lamp for 5 minutes at a distance of 15 cm. The tubing was rinsed with deionized water with gentle rubbing.

The lubricity and wettability of the tubing piece was examined by rubbing the silicone tubing by hand. The tubing appeared lubricious. Next, the silicone tubing piece was dipped in Congo red stain for the presence of the coating as previously described in Example 4. The visible indication of Congo red in the coating layer showed silicone tubing coated with POMA-BP polymer primer coating layer retained a coating of Lubricent™.

Example 12

A Comparative Example. Synthesis of Poly(maleic anhydride-alt-1-octadecene)silane (POMA-S)

A 5.0174 g amount of Poly(maleic anhydride-alt-1-octadecene) (POMA) (Aldrich Chemicals. Milwaukee, Wis.) was added to a 250 round-bottomed one-neck flask equipped with a stir bar, reflux condenser and drying tube. 6 ml of 3-aminopropylmethylbis(trimethylsiloxy)silane (S) (Gelest Inc., Morrisville, Pa.) and 0.0871 g of 4-(dimethylaminopyridine) and 100 ml of chloroform were then added to the flask and stirred. The reaction was stirred and refluxed at 83° C. in an oil bath for 2 hours, and the solvent was removed with a rotary evaporator.

The residue was dissolved in 50 ml chloroform and was washed with three times with 50 ml of 1N hydrochloric acid aqueous solution and three times with 50 ml of deionized water. The organic layer was dried with sodium sulfate, filtered and concentrated to dryness as described in Example 1. The solid had a white color.

Example 13

A Comparative Example. Coating Silicone with POMA-S

A piece of 10 cm silicone tubing was cleaned with isopropanol and dried. The silicone tubing piece was dipped into a coating solution including 60 mg/mL POMA-S in isopropanol (prepared as described in Example 12 above) at a speed of 1 cm/sec with a dwelling time of 30 seconds. The tubing was extracted from the coating solution, dried and illuminated under a UVM 400 ultraviolet lamp for 1 minute at a distance of 15 cm.

The POMA-S coated silicone tubing piece was dipped into a coating solution of Lubricent™ at a speed of 1 cm/sec with a dwelling time of 30 seconds, and then illuminated under a UVM 400 ultraviolet lamp for 5 minutes. The tubing was rinsed with deionized water with gentle rubbing.

The lubricity and wettability of the tubing piece was examined by rubbing the silicone tubing by hand. The tubing was not lubricious. Next, the piece was dipped in Congo red stain (Aldrich Chemicals, Milwaukee, Wis.) for the presence of the coating as previously described as described in Example 4. The absence of Congo red staining in the coating layer showed silicone tubing primed with POMA-S did not retain a coating of Lubricent™.

Example 14

A Comparative Example. Synthesis of Poly(methyl vinyl ether-alt-maleic anhydride) (PMVEMA-BP)

A 5.0185 g amount of Poly(methyl vinyl ether-alt-maleic anhydride) (PMVEMA) (Aldrich Chemicals, Milwaukee, Wis.) was added to a 1 L round-bottomed one-neck flask equipped with a stir bar, reflux condenser and drying tube. A 10.5127 g of amount of 4-(aminobenzophenone) (BP) and 0.0875 g of 4-(dimethylaminopyridine), 250 ml of chloroform and 650 ml of acetone (Fisher Chemicals, Pittsburgh, Pa.) were then added to the flask and stirred. The reaction was stirred and refluxed at 83° C. in an oil bath for 3 hours with argon, and the solvent was removed with a rotary evaporator.

The residue was dissolved in 50 mL acetone, and precipitated in 600 mL 1N hydrochloric acid aqueous solution using an electric overhead stirrer (Arrow Engineering, Hillside, N.J.) with a Teflon® shaft (Arrow Engineering, Hillside, N.J.) and propeller (Arrow Engineering, Hillside, N.J.). The solid was filtered, washed three times with 600 ml deionized water for 10 minutes using the electric overhead stirrer with the Teflon shaft and propeller. The product was lyophilized overnight and had a yellow color.

Example 15

A Comparative Example. Coating Silicone with PMVEMA-BP

A piece of 10 cm silicone tubing was cleaned with isopropanol and dried. The silicone tubing piece was dipped into a coating solution including 60 mg/mL PMVEMA-BP in isopropanol (prepared as described in Example 14 above) at a speed of 1 cm/sec with a dwelling time of 30 seconds. The tubing was extracted from the coating solution, dried and illuminated under a UVM 400 ultraviolet lamp for 1 minute at a distance of 15 cm.

The PMVEMA-BP coated silicone tubing piece was dipped into a coating solution of Lubricent™ at a speed of 1 cm/sec with a dwelling time of 30 seconds, and then illuminated under a UVM 400 ultraviolet lamp for 5 minutes. The tubing was rinsed with deionized water with gentle rubbing.

The lubricity and wettability of the tubing piece was examined by rubbing the silicone tubing by hand. The tubing was not lubricious. Next, the piece was dipped in Congo red stain for the presence of the coating as previously described in Example 4. The presence of Congo red staining in the coating layer showed silicone tubing primed with PMVEMA-BP retained a coating of Lubricent™ although the coating was not lubricious.

Example 16

Passivating Coating Based Upon Polyzwitterionic Brush Coating

For this Example, twelve (12) mm glass coverslips were coated with polydimethylsiloxane (PDMS), cured, and then coated with BP-POMAS, followed by application of a passivating coating, a polySBMA zwitterionic graft. Passivation against cellular attachment and proliferation was tested using E18 rat brain cortical cultures (mixed cultures).

Prior to application of a coating, substrates were cleaned as follows. 12 mm glass coverslips (VWR micro coverglass, 12 mm circles, No. 2) were immersed in isopropyl alcohol (IPA) and sonicated for 15 minutes. The coverslips were then placed on a rocker for 5 minutes.

A silicone surface was provided to the cleaned coverslips as follows. Sylgard 184 elastomer (Dow Corning) was combined with PDMS to provide a 10:1 ratio (100 µL elastomer was used for every 1 g PDMS). The elastomer was mixed, and vacuum was applied for 10-15 minutes. Elastomer was placed on the coverslips by pipetting a 50 µL drop on the center of the coverslip. Vacuum was applied for 10 additional minutes.

Coated coverslips were placed on a hotplate, at 60° C. for one hour. After curing, the coated substrates were incubated at ambient conditions overnight.

Siliconized coverslips were coated with a primer composition as follows. Siliconized coverslips were immersed into a solution of Photo-POMAS in IPA (20 g/L, prepared as described above in Example 1), for 30 seconds, then extracted and spin-dried at a rate of approximately 650 rpm for 10 seconds to produce an even coating. After removal from the Photo-POMAS solution, substrates were allowed to air dry further for 5 minutes. Subsequently, substrates were illuminated with ultraviolet light (Harland Medical UVM400, Eden Prairie, Minn.) (300 to 400 nm) for 3 minutes at a distance of 12 cm from the light source. After illumination, the coated substrates were allowed to cool.

The photo-POMAS coated coverslips were then treated with a photochemical crosslinker prepared as described in Example 1 of U.S. Pat. No. 7,772,393. Treatment was accomplished by depositing 20 microliters of a 10 mg/mL solution of the crosslinker in acetone to each disc. The treated coverslips were allowed to air-dry in the dark for 30 minutes prior to being placed face-down in a modified 15 mL polypropylene test tube with the tip cut off and notches cut out of the bottom. The modified test tubes were used to securely hold and submerge the primed discs in a quartz chamber filled with zwitterionic monomer.

Next, a zwitterionic polymer was grafted from the surface of the coated substrates as follows. A monomer solution of [3-(methacryloylamino)propyl]-dimethyl(3-sulfopropyl) ammonium hydroxide, inner salt (Aldrich), was prepared at a concentration of 0.5 M in deionized water (13.642 g of SBMAAm monomer and 93.3 mL deionized water) and sparged with argon gas for 20 minutes. 10 mL of 0.5 M SBMAAm monomer solution was then added to test tubes containing the substrates. The quartz chamber was purged with argon gas for five minutes prior to being sealed with black vinyl tape (3M). The sealed quartz chamber containing the primed samples was placed 10 cm above the ultraviolet light source (Harland Medical UVM400, Eden Prairie, Minn.) and illuminated for 30 minutes. The post-graft polymerized samples were removed and washed with copious amounts of deionized water before being rinsed with isopropanol and allowed to air-dry. The success of the graft polymerization was confirmed by the observed low water contact angle.

Subsequent evaluation of the coated samples demonstrated superior passivation to dissociated rat brain culture (cellular attachment and proliferation) versus bare silicone.

Example 17

Synthesis of Perfluorophenylazide-Poly(octadecene-alt-maleic anhydride)silane and Coating for Silicone Tubing (Perfluorophenylazide-POMAS)

Five grams of poly(octadccene-alt-maleic anhydride) (MW 30K to 50K), (Aldrich Chemical Company, WI), 0.20 g of perfluoroaniline (Aldrich Chemical Company, WI), and 0.08 g 4-dimethylaminopyridine (Aldrich) will be dissolved in chloroform and refluxed under argon for 2 hrs, reaction cooled to room temperature. A 5 mL aminopropylmethyl bis(trimethyl-siloxy) silane portion will be added and reaction refluxed for another 2 hours. The resulting solution is washed 3 times with 2N HCl, followed by 3 washes with deionized water. The sample is dried over $Na_2SO_4$. After vacuum filtration, the filtrate is concentrated to dryness on a rotovap. The sample is then refluxed for 8 hours in a mixture of 0.33 g NaN₃ a water/acetone mixture to obtain the product shown below. See Keana, John F. W. et al., "New Reagents for Photoaffinity Labeling: Synthesis and Photolysis of Functionalized Perfluorophenyl Azides," J. Org. Chem. 55: 3640-3647 (1990).

Coatings are applied to the substrate by immersing the substrate in the coating solution, removing the substrate from the solution and after drying, the coated substrate is heated to 140° C. for 5 to 30 minutes to crosslink the coating.

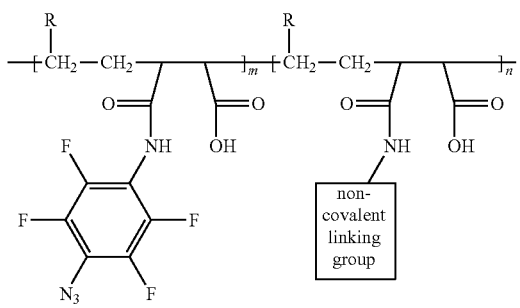

R represents 16 carbon hydrocarbon chain.

Example 18

Coating with Perfluorophenylazide-POMAS

Perfluorophenylazide is a latent reactive group that generates perfluorophenyl nitrenes that undergo C—H/N—H insertion and alkene addition reactions. Perfluorophenyl azide can be activated either by UV illumination or by heating. Thermally initiated insertion reactions are reported to take place at temperatures typically ≥130°. In order to provide a coating on a surface of silicone, the silicone substrate is immersed in the perfluorophenylazide-POMAS polymer in a suitable solvent, for a suitable time. The substrates are then extracted from the coating solution at a suitable rate (for example, 0.5 cm/second), then air dried. Subsequent to drying, the substrates are heated to a temperature suitable to activate the perfluorophenylazide latent reactive groups. Patterning can be accomplished by first selectively activating a portion of the latent reactive groups on the coated substrate with UV light (for example, utilizing a mask) and subsequently reacting the remaining latent reactive groups with either UV light or heat under substantially different conditions.

Example 19

Incorporation of Passivating PEG Groups as Part of Polymer Composition

Five grams of poly(octadecene-all-maleic anhydride) (MW 30K to 50K), (Aldrich Chemical Company, WI), 0.12 g of perfluoroaniline (Aldrich Chemical Company, WI), and 0.08 g 4-dimethylaminopyridine (Aldrich) are dissolved in chloroform and refluxed under argon for 2 hours. The reaction is cooled to room temperature and 14 g of methoxy-polyethylene glycol amine (MW 2000 Aldrich) is then added. The reaction is then refluxed under argon for 2 hours and cooled to room temperature. Subsequently, a 2.5 mL aminopropylmethyl bis(trimethyl-siloxy) silane portion is added and the reaction is then refluxed for another 2 hours.

The resulting solution is washed 3 times with 2N HCl, followed by 3 washes with deionized water. The sample is dried over Na₂SO₄. After vacuum filtration, the filtrate is concentrated to dryness on a rotovap. The sample is refluxed for 8 hours in a mixture of 0.33 g NaN₃ a water/acetone mixture to obtain the product shown below.

Coatings are applied to the substrate by immersing the substrate in the coating solution, removing the substrate from the solution and after drying, the coated substrate is heated to 140° C. for 5 to 30 minutes to crosslink the coating.

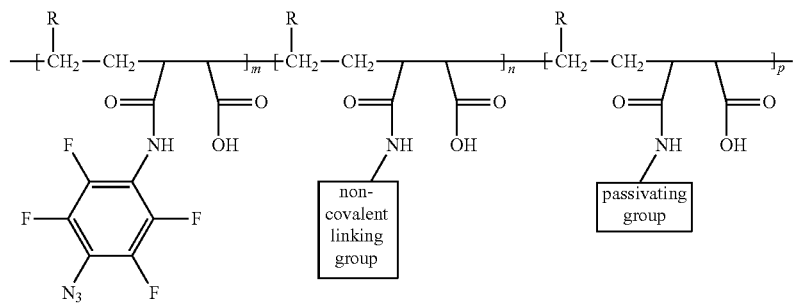

R represents 16 carbon hydrocarbon chain.

Example 20

Polymer Including Noncovalent Linking Group, Perfluorophenylazide-POMAS and Initiator (ATRP Initiator)

Five grams of poly(octadecene-alt-maleic anhydride) (MW 30K to 50K), (Aldrich Chemical Company, WI), 0.12 g of perfluoroaniline (Aldrich Chemical Company, WI), and 0.08 g 4-dimethylaminopyridine (Aldrich) are dissolved in chloroform and refluxed under argon for 2 hours. The reaction is cooled to room temperature and 1.32 g of N-Boc-1,4-butanediamine (Aldrich Chemical Company, WI) is added. The reaction is refluxed under argon for 2 hours, cooled to room temperature and 2.7 mL of trifluoroacetic acid is added. The reaction is then refluxed for 2 hours and to achieve deprotection of the amine. The sample is then washed with 0.5N NaOH, followed by wash with deionized water and drying on rotary evaporator. The sample is then dissolved in chloroform, cooled to 0° C. and 0.9 mL of α-bromoisobutyryl bromide (Aldrich Chemical Company, WI) and 1 mL triethylamine is added. The reaction is run for 2 hours. Subsequently, a 2.5 mL aminopropylmethyl bis(trimethyl-siloxy) silane portion is added, and the reaction is refluxed for 2 hours. The resulting solution is washed 3 times with 2N HCl, followed by 3 washes with deionized water. The sample is then dried over $Na_2SO_4$. After vacuum filtration, the filtrate is concentrated to dryness on a rotovap The sample is refluxed for 8 hours in a mixture of 0.33 g $NaN_3$ a water/acetone mixture to obtain the product shown below.

Coatings are applied to the substrate by immersing the substrate in the coating solution, removing the substrate from the solution and after drying, the coated substrate is heated to 140° C. for 5 to 30 minutes to crosslink the coating.

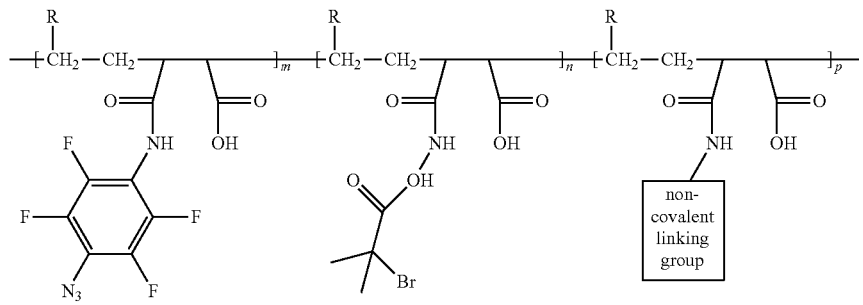

Example 21

Polyzwitterionic Graft

The polymer of example 20 is prepared as a coating solution by dissolving the polymer in isopropanol or other suitable solvent. Silicone coupons are immersed in the coating solution and withdrawn to achieve a thin layer of the polymer on the surface of the silicone coupon.

Surface-initiated polymerization of the zwitterionic monomers occurs as follows. Bipyridine (0.039 g) is dissolved in water (18 mL), sparged with argon, transferred to an argon-purged tube containing CuCl (0.002 g) and $CuCl_2$ (0.015 g). The mixture is stirred until no trace of copper powder is observed. Next, [3-(methacryloylamino)propyl]-dimethyl(3-sulfopropyl)ammonium hydroxide, inner salt (Aldrich), is added and all components are immediately transferred into an argon-purged tube containing the coated silicone coupon. The polymerization is carried out at 30° C. for 4 hours. The substrate is then rinsed three times with water and three times with IPA. Thermal crosslinking of the coating is achieved by heating to 140° C. from 5 to 30 minutes, or photo crosslinking of the coating is achieved by exposure to UV light source (Harland Medical UVM400, Eden Prairie, Minn.). See also Ohno, K., et al., "A Versatile Method of Initiator Fixation for Surface-Initiated Living Radical Polymerization on Polymeric Substrates," Macromolecules 43: 5569-5574 (2010).

Example 22

Synthesis of Acetonide-Protected Dopamine

Dopamine was synthesized and protected in preparation for adding dopamine as a noncovalent linking group to a polymer.

A. N-Protection of Dopamine.

10.48 g of 3-hydroxytyramine hydrochloride (Aldrich Chemicals, Milwaukee, Wis.) was dissolved in 100 ml of 10 mM borax buffer, then 30 ml of THF was added. After the THF addition, a solution of 9 ml of benzylchloroformate (Aldrich Chemicals, Milwaukee, Wis.) in 70 ml THF was added dropwise. Approximately 30 g of borax was added to maintain the pH above 7. After addition of the benzylchloroformate was complete, the reaction mixture refluxed overnight. Upon cooling, the reaction mixture was added to 200 ml of chloroform, 200 ml of 1M NaCl aqueous solution, and 100 ml of deionized water. The organic phase was separated and dried over sodium sulfate, then the solvent was removed by rotary evaporation to give 9.83 g of crude material. The product was further purified by column purification with 90:10 dichloromethane:acetone to yield 9.16 g N-carboxybenzyldopamine.

The product was characterized by $^1$H NMR (DMSO-d6): 8.70 ppm (s, br, 2H), 7.32 ppm (m, 5H), 6.60 ppm (m, 2H), 6.42 ppm (m, 1H), 5.01 ppm (s, 2H), 3.12 ppm (m, 2H), 2.50 ppm (m, 2H). The reaction scheme was as follows:

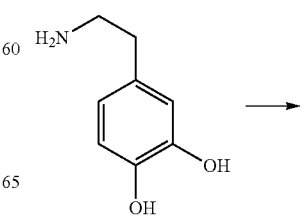

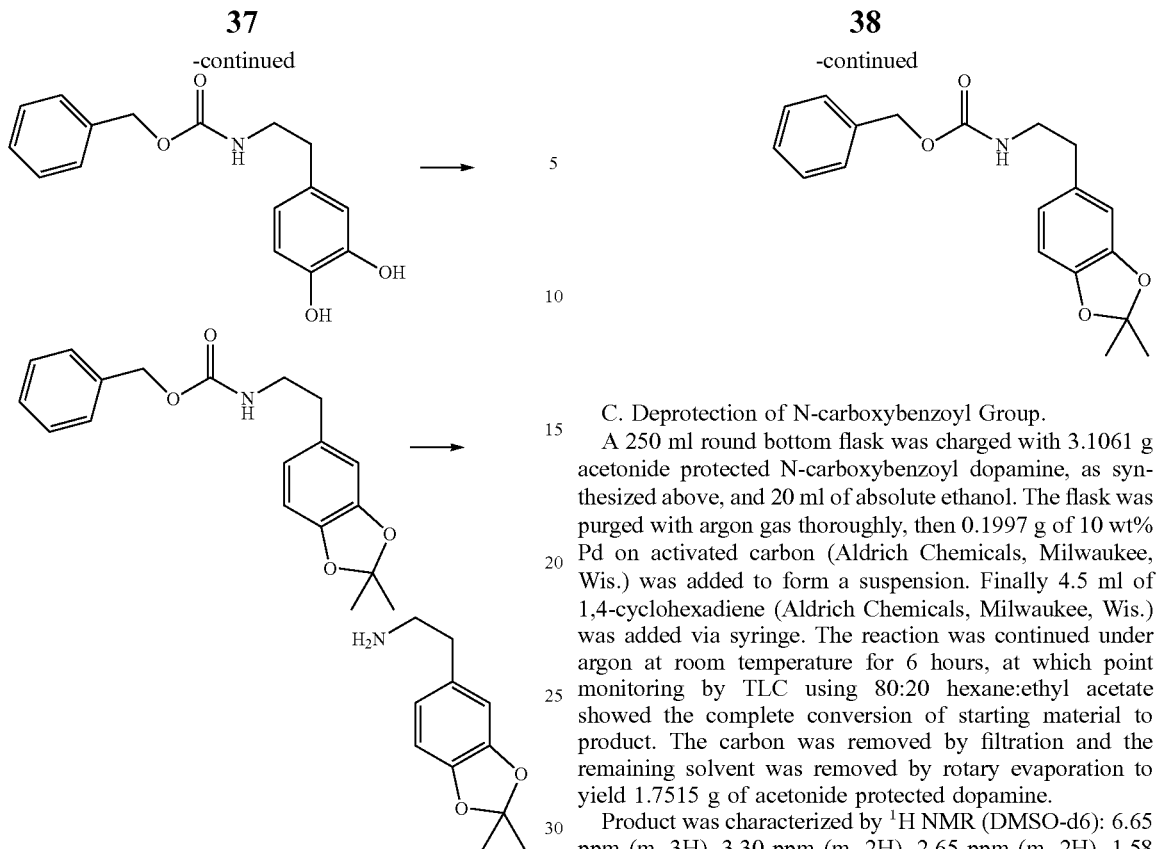

B. Acetonide Protection of Catechol Moiety.

4.68 g N-carboyxbenzoyldopamine, synthesized as described above, was dissolved in 250 ml THF. 0.2401 g p-toluenesulfonic acid (Aldrich Chemicals, Milwaukee, Wis.) was added, followed by 41 ml of 2,2-dimethoxypropane (Aldrich Chemicals, Milwaukee, Wis.). The reaction vessel was equipped with a sohxlet extractor with 4 A molecular sieves as a drying agent in the sohxlet extraction filter cup. The reaction mixture refluxed through the sohxlet extractor overnight. After cooling, the reaction mixture was concentrated by rotary evaporation, then diluted with 100 ml chloroform and washed with two 100 ml aliquots of deionized water. The organic layer was then dried over sodium sulfate, filtered, concentrated by rotary evaporation to yield 8.31 g of crude product. This was further purified by column chromatography using 80:20 hexane:ethyl acetate as an eluent. Yield: 2.12 g.

The product was characterized by $^1$H NMR (DMSO-d6): 7.32 ppm (m, 5H), 6.66 (d, 2H), 6.58 ppm (d, 1H), 5.01 ppm (s, 2H), 3.18 ppm (m, 2H), 2.58 ppm (m, 2H), 1.57 ppm (s, 6H). Reaction scheme was as follows:

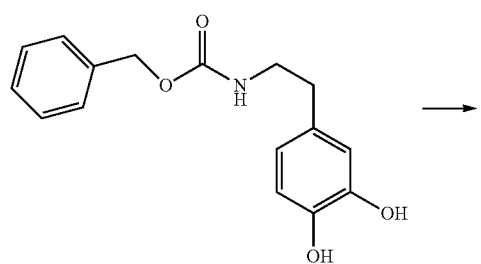

C. Deprotection of N-carboxybenzoyl Group.

A 250 ml round bottom flask was charged with 3.1061 g acetonide protected N-carboxybenzoyl dopamine, as synthesized above, and 20 ml of absolute ethanol. The flask was purged with argon gas thoroughly, then 0.1997 g of 10 wt% Pd on activated carbon (Aldrich Chemicals, Milwaukee, Wis.) was added to form a suspension. Finally 4.5 ml of 1,4-cyclohexadiene (Aldrich Chemicals, Milwaukee, Wis.) was added via syringe. The reaction was continued under argon at room temperature for 6 hours, at which point monitoring by TLC using 80:20 hexane:ethyl acetate showed the complete conversion of starting material to product. The carbon was removed by filtration and the remaining solvent was removed by rotary evaporation to yield 1.7515 g of acetonide protected dopamine.

Product was characterized by $^1$H NMR (DMSO-d6): 6.65 ppm (m, 3H), 3.30 ppm (m, 2H), 2.65 ppm (m, 2H), 1.58 ppm (s, 6H). Reaction scheme was as follows:

Example 23

Addition of Acetonide-Protected Dopamine to 6-Maleimido-Hexanoylchloride 6-maleimidohexanoic acid was synthesized according to the procedure described in U.S. Pat. No. 6,456,178 example 4. A 250 ml roundbottom flask was charged with 1.0297 g of 6-maleimidohexanoic acid and 25 ml of anhydrous chloroform under an argon atmosphere. To this flask, 1 ml of oxalic chloride (Aldrich Chemicals, Milwaukee, Wis.) was added via syringe. The reaction mixture stirred overnight at room temperature under argon. After 24 hours, the solvent was removed in vacuo and the resulting 6-maleimidohexanoyl chloride was washed twice with hexane, with hexane removal in vacuo. The acid chloride was then dissolved in 15 ml of anhydrous chloroform under an argon atmosphere and added dropwise to a solution of 0.9678 g of acetonide-protected dopamine (as synthesized from Example 22 above) in 10 ml anhydrous chloroform with 0.75 ml triethylamine. The reaction mixture stirred at 0° C. overnight under an argon atmosphere. The resulting white precipitate was then filtered off, and the solvent removed by rotary evaporation to yield 2.7249 g of 2,2-dimethyl(1,3) benzodioxole-ethyl, 6-maleimidohexanoamide.

Product was characterized by $^1$H NMR (DMSO-d6): 7.82 ppm (m, 1H), 6.98 ppm (s, 2H), 6.64 ppm (m, 2H), 6.57 ppm (m, 1H), 3.35 ppm (m, 2H), 3.15 ppm (m, 2H), 2.55 ppm (m, 2H), 1.99 ppm (m, 2H), 1.58 ppm (s, 6H), 1.43 ppm (m, 6H). Reaction scheme was as follows:

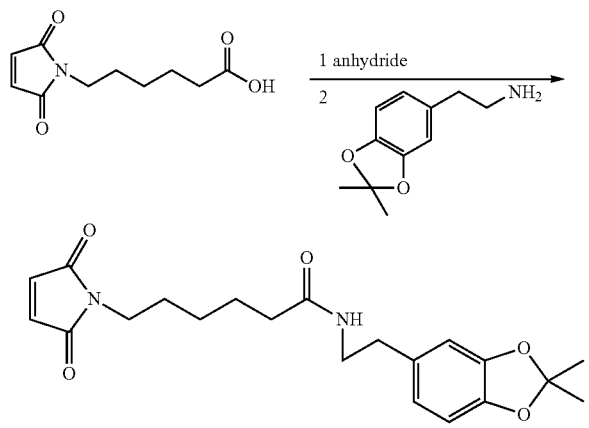

Example 24

Copolymerization of Mal-Hex-Dopamine-Acetonide with Maleic Anhydride

Copolymerization of Mal-Hex-Dopamine-Acetonide with Maleic Anhydride was accomplished as follows. 0.2481 g of 2,2-dimethyl(1,3)benzodioxole-ethyl, 6-maleimidohexanoamide, as synthesized in Example 23 above, was dissolved in 3 ml of tetrahydrofuran in a 20 ml amber jar. To this, 0.3529 g of recrystallized maleic anhydride (Aldrich Chemicals. Milwaukee, Wis.) and 0.0166 g of AIBN was added. The reaction mixture was sparged with argon for 5 minutes, then sealed and heated to 65° C. overnight. The reaction mixture was cooled to room temperature. TLC with 90:10 chloroform:acetone revealed no starting maleic anhydride or 2,2-dimethyl(1,3)benzodioxole-ethyl, 6-maleimidohexanoamide remained. The remaining THF was removed by air stream, then the crude copolymer was dissolved in 95:5 trichloroacetic acid:water to deprotect the catechol. The copolymer stirred at room temperature overnight in the TCA:water mixture, then was precipitated in diethyl ether at room temperature. A brown viscous material was obtained, yield: 0.4216 g.

Polymer product was characterized by $^1$H NMR (DMSO-d6): 7.82 ppm (m), 6.67 ppm (s), 6.50 ppm (m), 3.70 (s, broad), 2.05 (s), 1.40 ppm (m, broad).

Example 25

Coating with Dopamine-Functionalized Maleic Anhydride Copolymer on HDPE and Silicone Three inch long segments of HDPE (Minnesota Medtec, rod stock 1/16 inch OD) and silicone tubing (Dow Silastic 80, medical grade 0.375 inch OD, 0.250 inch ID) were cleaned by wiping with isopropanol. The pieces were then coated with a solution of the dopamine-functionalized maleic anhydride copolymer, as synthesized in Example 24 above, at 10 mg/ml in isopropanol. Pieces were immersed in the solution for 30 seconds, then extracted at a rate of 0.5 cm/sec and air dried for one hour.

The coating was visualized by staining with 0.3% Crystal Violet gram stain for 10 seconds, followed by rinsing in a water stream. All of the pieces showed a coating line were the coating was applied as evidenced by a purple color. Uncoated silicone and HDPE did not develop any purple stain. Results demonstrated the affinity of the coating on HDPE and silicone substrates.

Example 26

Synthesis of Benzophenone Functionalized Maleimidohexanamide

A 250 ml round bottom flask was charged with 6.0291 g of 4-aminobenzophenone (Aldrich Chemicals, Milwaukee, Wis.) and 25 ml of anhydrous chloroform under an argon atmosphere. To this, 4 ml of triethylamine was added. The reaction mixture was cooled to 0° C. with an ice bath and a solution of 5.4370 g 6-maleimidohexanoyl chloride, as prepared in Example 23 above in 25 ml anhydrous chloroform was added dropwise. The reaction stirred overnight under argon at 0° C. A white precipitate formed and was removed by gravity filtration, then the solvent was removed by rotary evaporation.

Product was characterized by $^1$H NMR (DMSO-d6): 7.53 ppm (m, 9H), 6.98 ppm (s, 2H), 2.33 ppm (m, 2H), 1.55 ppm (m, 4H), 1.27 (m, 2H). Reaction scheme was as follows:

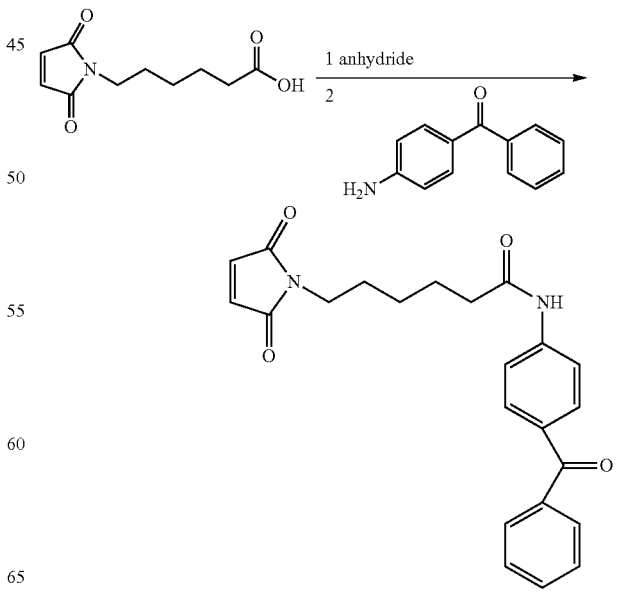

Example 27

Copolymerization of Monomer Containing Latent Reactive Group with Monomer Containing Linking Group and Vinylpyrrolidone 0.5110 g of 2,2-dimethyl(1,3)benzodioxole-ethyl, 6-maleimidohexanoamide, as synthesized in Example 23 above, was dissolved in 3 ml of tetrahydrofuran in a 20 ml amber jar. To this, 0.1100 g of 4-benzophenone 6-maleimidohexanamide, as synthesized as in Example 26 above, and 0.752 ml of vinylpyrrolidone (Aldrich Chemicals, Milwaukee, Wis.) was added under argon atmosphere. Finally, 0.0435 g AIBN and 0.010 ml of N,N,N',N'-tetramethylenediamine (Aldrich Chemicals, Milwaukee, Wis.) was added. The reaction mixture was sparged with argon for 5 minutes, then sealed and heated to 65 C overnight. The reaction mixture was cooled to room temperature, then precipitated in ethyl acetate, and washed twice with more ethyl acetate, to give a yellow polymer, yield: 0.6987 g.

The polymer product was characterized by $^1$H NMR (DMSO-d6): 7.5-7.8 ppm (m, broad), 6.65-6.75 ppm (s, broad), 2.8-3.8 ppm (m, broad), 2.4-0.8 ppm (m, broad), 1.58 ppm (s, broad).

Example 28

Deprotection of Acetonide on Pendent Dopamine, Pendent Benzophenone VP Copolymer The 0.6987 g of acetonide-protected dopamine, benzophenone vinyl pyrrolidone copolymer synthesized in Example 27 was dissolved in 20 ml of 95:5 trichloroacetic acid:deionized water and stirred overnight at room temperature. After 24 hours the reaction mixture was precipitated in cold deionized water, then washed with cold deionized water and dried on filter paper, yield: 0.2316 g of polymer.

Polymer product was characterized by $^1$H NMR (DMSO-d6): 8.7 ppm (d, broad) 7.4-7.8 ppm (m, broad), 6.5-6.7 ppm (m, broad), 6.3-6.45 ppm (m, broad), 2.8-3.8 ppm (m, broad), 2.4-0.8 ppm (m, broad).

Example 29

Synthesis of Maleic Anhydride Copolymer Containing Noncovalent Linking Groups and Latent Reactive Groups A coating agent composed of a polymer including a polymaleic acid derivative, pendent noncovalent linking groups, and pendent latent reactive groups is synthesized as follows. 0.25 g of 2,2-dimethyl(1,3)benzodioxole-ethyl, 6-maleimidohexanoamide, as synthesized in Example 24, is dissolved in 3 ml of tetrahydrofuran in a 20 ml amber jar. Similarly, 0.15 g of benzophenone-functionalized maleimidohexanamide, as synthesized in Example 27 is dissolved in 2 ml of tetrahydrofuran, then added to the 2,2-dimethyl(1,3)benzodioxole-ethyl, 6-maleimidohexanoamide solution. To this, 0.35 g of recrystallized maleic anhydride (Aldrich Chemicals, Milwaukee, Wis.) and 0.02 g of AIBN is added. The reaction mixture is sparged with argon for 5 minutes, then sealed and heated to 65 C overnight. The reaction mixture is cooled to room temperature. The remaining THF is removed by air stream, then the crude copolymer is dissolved in 95:5 trichloroacetic acid:water to deprotect the catechol. The copolymer is stirred at room temperature overnight in the TCA:water mixture, then is precipitated in diethyl ether at room temperature to yield a copolymer including a polymaleic acid derivative having pendent benzophenone and dopamine groups.

What is claimed is:

1. A method for forming a coated article, the method comprising steps of (a) applying a base coating composition to a surface of the article, the base coating composition comprising a polymer that includes a polymaleic acid derivative or a copolymer of a polymaleic acid derivative, one or more photoreactive groups that are pendent from the polymer, and one or more siloxane groups; and (b) exposing the base coating composition to actinic energy, thereby activating at least some of the photoreactive groups and covalently coupling the base coating composition on the surface.

2. The method according to claim 1 wherein the surface of the article is not pretreated by chemical, biological or physical pretreatments that generate reactive groups on the surface prior to applying the base coating composition to the surface.

3. The method according to claim 1 further comprising a step of applying one or more overcoat layers onto the base coating composition.

4. The method according to claim 1 wherein step (a) comprises applying a base coating composition comprising a polymer that includes a polymaleic acid derivative or a copolymer of a polymaleic acid derivative, one or more photoreactive groups that are pendent from the polymer, and one or more amide siloxane groups.

5. The method according to claim 1 further comprising a step of disposing an active agent coating layer on the base coating composition.

6. The method according to claim 5 wherein the step of disposing an active agent coating layer is performed after step (b).

7. A coated article prepared by the method of claim 1 wherein the base coating composition does not exhibit hydrophobic recovery.

8. A coated article prepared by the method of claim 2, wherein the article is a medical device.

9. A coated article prepared by the method of claim 3, wherein one or more overcoat layers comprises a lubricious polymer.

10. The coated article according to claim 9 wherein the one or more overcoat layers retain a lubricity while hydrated, lubricity being measured in grams of force when the coated article is subjected to a friction test, the friction test comprising fifteen cycles, each cycle comprising steps of: (a) compressing silicone pads against the article; (b) pulling the article upward between the silicone pads, (c) releasing the silicone pads, allowing the article to move freely downward, (d) measuring friction force required to pull the article upwards through the silicone pads after each testing cycle, and (e) comparing the friction force measured in (d) across the fifteen cycles.

11. An article comprising a substrate and a multilayer coating comprising a base coating layer and an overcoat layer, wherein the base coating layer comprises (a) a polymaleic acid derivative or a copolymer thereof, (b) one or more aryl ketones; and (c) one or more sihoxane groups having a formula:

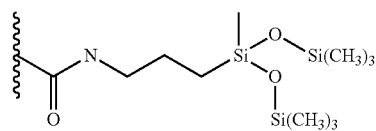

wherein wavy lines represent the polymaleic acid derivative, and wherein the overcoat layer comprises active agent.

12. The article according to claim 11 wherein the article is a medical device.

13. The article according to claim 11 wherein the active agent is selected from anti-microbial, anti-fouling, anti-angiogenic, angiogenic, antifibrotic, fibrotic, anti-thrombosis, and protein resistant agents, and combinations of any two or more of these.

14. An article comprising a substrate and a base coating disposed on a surface of the substrate, the base coating comprising: (a) a polymer that includes a polymaleic acid derivative; (b) one or more photoreactive groups that are pendent from the polymer; and (c) one or more siloxane groups.

15. The article according to claim 14 wherein the base coating composition does not exhibit hydrophobic recovery.

16. The article according to claim 14 wherein the substrate is fabricated from a material selected from silicon; silicone; polyolefin; polyethylene; polypropylene; vinyl polymer; polystyrene; polyacrylate; polymethacrylate; poly (methyl)methacrylate; poly(vinylacetate); poiy(vinyi alcohol); chlorine-containing polymer; polyoxymethylene; polycarbonate; polyamide; polyimide; polyurethane; phenolics; amino-epoxy resin; polyester; cellulose-based plastic; rubber-like plastic; aluminum, chromium, cobalt, iron, tantalum, titanium, and alloys thereof; nitinol and other nickel-titanium alloys; stainless steel; noble metals; and cobalt-chromium, and combinations of any two or more of these.

17. The article according to claim 14 wherein the polymaleic acid derivative is a derivatized poly(alkene-co-maleic anhydride).

18. The article according to claim 14 further comprising an overcoat layer disposed on the base coating.

19. The article according to claim 18 wherein the overcoat layer comprises active agent.

20. The article according to claim 19 wherein the active agent is selected from anti-microbial, anti-fouling, anti-angiogenic, angiogenic, antifibrotic, fibrotic, anti-thrombosis, and protein resistant agents and combinations of any two or more of these.

* * * * *

UNITED STATES PATENT AND TRADEMARK OFFICE
CERTIFICATE OF CORRECTION

PATENT NO. : 9,539,371 B2  
APPLICATION NO. : 14/749815  
DATED : January 10, 2017  
INVENTOR(S) : Wen et al.

Page 1 of 1

It is certified that error appears in the above-identified patent and that said Letters Patent is hereby corrected as shown below:

In Claim 16, at Column 44, Line 1, after "(methyl)methacrylate;" insert --polyacrylonitrile;--; and "poiy(vinyi alcohol)" should read --poly(vinyl alcohol)--

Signed and Sealed this  
Twenty-first Day of March, 2017

Michelle K. Lee  
*Director of the United States Patent and Trademark Office*